(12) United States Patent
Nammalwar et al.

(10) Patent No.: US 10,406,219 B2
(45) Date of Patent: Sep. 10, 2019

(54) **MULTIVALENT *BRUCELLA* VACCINE FOR PROTECTION AGAINST MYCOBACTERIAL INFECTIONS AND METHODS OF USING THE SAME**

(71) Applicant: VIRGINIA TECH INTELLECTUAL PROPERTIES, INC., Blacksburg, VA (US)

(72) Inventors: Sriranganathan Nammalwar, Blacksburg, VA (US); Hamzeh Al Qublan, Blacksburg, VA (US); Garrett Smith, Blacksburg, VA (US); Stephen Boyle, Blacksburg, VA (US); Gerhardt Schurig, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 111 days.

(21) Appl. No.: 15/509,381

(22) PCT Filed: Sep. 8, 2015

(86) PCT No.: PCT/US2015/048841
§ 371 (c)(1),
(2) Date: Mar. 7, 2017

(87) PCT Pub. No.: WO2016/040258
PCT Pub. Date: Mar. 17, 2016

(65) Prior Publication Data
US 2017/0246282 A1 Aug. 31, 2017

Related U.S. Application Data

(60) Provisional application No. 62/047,945, filed on Sep. 9, 2014.

(51) Int. Cl.
| | |
|---|---|
| *A61K 39/04* | (2006.01) |
| *A61K 45/06* | (2006.01) |
| *A61K 35/74* | (2015.01) |
| *C07K 14/35* | (2006.01) |
| *C12N 1/20* | (2006.01) |
| *C12N 15/74* | (2006.01) |
| *A61K 39/00* | (2006.01) |

(52) U.S. Cl.
CPC .............. *A61K 39/04* (2013.01); *A61K 35/74* (2013.01); *A61K 45/06* (2013.01); *C07K 14/35* (2013.01); *C12N 1/20* (2013.01); *C12N 15/74* (2013.01); *A61K 2039/523* (2013.01); *A61K 2039/552* (2013.01); *A61K 2039/70* (2013.01)

(58) Field of Classification Search
None
See application file for complete search history.

(56) References Cited

U.S. PATENT DOCUMENTS

2010/0183677 A1  7/2010  Skeiky et al.

OTHER PUBLICATIONS

Rojas, "*Bruclla abortus* RB51 Vaccine: Testing its Spectrum of Protective and Curative Characteristics", Ph.D. Thesis, 20034.
Rajasekaran et al., "*Brucella abortus* strain RB51 leucine auxotroph as an environmentally safe vaccine for plasmid maintenance and antigen overexpression", Appl Environ Microbiol, 2008, pp. 7051-7055, vol. 74, No. 22.
Aagaard et al., "Protection and polyfunctional T cells induced by Ag85B-TB10.4/IC31 against *Mycobacterium tuberculosis* is highly dependent on the antigen dose", PLOS One, 2009, p. e59, vol. 4, No. 6.
Seleem et al., "Activity of native vs. synthetic promoters in *Brucella*", FEMS Microbiol Lett, 2008, pp. 211-215, vol. 288, No. 2.
Parida et al., "Novel Bacterial Delivery System with Attenuated *Salmonella typhimurium* Carrying Plasmid Encoding Mtb Antigen 85A for Mucosal Immunization", Ann. N.Y. Acad. Sci. 1056: 366-378 (2005).
Weiner et al., "Recent advances towards tuberculosis control: vaccines and biomarkers", Journal of Internal Medicine 275: 467-480 (2014).

*Primary Examiner* — Brian Gangle
(74) *Attorney, Agent, or Firm* — W & C IP

(57) ABSTRACT

Provided herein is a multivalent *Brucella* vaccine expressing at least one heterologous *M. tuberculosis* antigen. The vaccines described herein serve as an environmentally safe bivalent vaccine for protection against *Brucella* and *Mycobacterium* infections simultaneously. In particular, a multivalent vaccine comprising a *Brucella* strain transformed with a vector that expresses at least one *M. tuberculosis* antigen, where the *M. tuberculosis* antigen(s) is codon optimized for the *Brucella* strain is provided. In some aspects, the *Brucella* strain is *B. abortus* strain RB51 leuB and the *M. tuberculosis* antigen is one or more of Ag85B, Rv2660c, and ESAT6.

24 Claims, 19 Drawing Sheets
Specification includes a Sequence Listing.

Figure 4A

IgG chart: OD at 450 nm vs Weeks post-innoculation (Week 3, Week 6)
- RB51-Rv2660c-ESAT6
- RB51FlgE-Rv2660c-ESAT6
- RB51
- Saline

Figure 4B

IgG2a chart: OD at 450 nm vs Weeks post-innoculation (Week 3, Week 6)
- RB51-Rv2660c-ESAT6
- RB51FlgE-Rv2660c-ESAT6
- RB51
- Saline

Figure 4C

IgG1 chart: OD at 450 nm vs Weeks post-innoculation (Week 3, Week 6)
- RB51-Rv2660c-ESAT6
- RB51FlgE-Rv2660c-ESAT6
- RB51
- Saline Esat6:SEQ ID NO:1
GGATCCATGACGGAACAGCAGTGGAATTTCGCCGGCATCGAAGCCGCCGCCTCCGCCATC
CAGGGCAATGTGACGAGCATCCATAGCCTCCTCGATGAAGGCAAGCAGTCGCTGACCAAG
CTTGCCGCGGCCTGGGGCGGCTCGGGCAGCGAAGCGTATCAGGGCGTCCAGCAGAAGT
GGGACGCGACCGCCACGGAACTTAACAATGCGCTCCAGAACCTGGCCCGCACGATCTCG
GAAGCGGGCCAGGCGATGGCGTCCACGGAAGGCAATGTCACGGGCATGTTCGCGAGATC
TTAATCTAGA.

Figure 13A

85B: SEQ ID NO:2
GGATCCTTCTCCCGCCCGGGCCTCCCGGTCGAATATCTCCAGGTTCCGTCCCCGAGCATGG
GCCGCGACATCAAGGTCCAGTTCCAGTCCGGCGGCAACAATTCGCCGGCCGTCTATCTGCT
TGACGGCCTTCGCGCGCAGGATGACTATAATGGCTGGGATATCAACACCCCGGCCTTCGAA
TGGTATTATCAGAGCGGCCTGTCCATCGTCATGCCGGTGGGCGGCCAGTCGAGCTTCTATTC
GGACTGGTATAGCCCGGCCTGCGGCAAGGCGGGCTGCCAGACCTATAAGTGGGAAACCCT
CCTGACGTCGGAACTCCCGCAGTGGCTGAGCGCCAATCGCGCGGTGAAGCCGACGGGCT
CCGCCGCGATCGGCCTCTCGATGGCCGGCTCCTCGGCGATGATCCTGGCCGCGTATCATCC
GCAGCAGTTCATCTATGCCGGCTCCCTGTCGGCGCTTCTCGACCCGAGCCAGGGCATGGGC
CCGTCCCTGATCGGCCTTGCCATGGGCGATGCGGGCGGCTATAAGGCCGCGGATATGTGG
GGCCCGAGCTCCGACCCGGCCTGGGAACGCAACGATCCGACCCAGCAGATCCCGAAGCTT
GTTGCCAACAATACCCGCCTCTGGGTCTATTGCGGCAACGGCACGCCGAATGAACTGGGC
GGCGCCAATATCCCGGCGGAATTCCTGGAAAATTTCGTGCGCTCGAGCAACCTTAAGTTCC
AGGATGCCTATAACGCCGCGGGCGGCCATAACGCGGTTTTCAATTTCCCGCCGAACGGCAC
GCACTCGTGGGAATATTGGGGCGCGCAGCTCAATGCCATGAAGGGCGACCTCCAGTCCTC
CCTCGGCGCGGGCAGATCTTAATCTAGA.

Figure 13B

RV2660c: SEQ ID NO:3
GGATCCGTTATCGCGGGCGTCGATCAGGCGCTTGCGGCCACGGGCCAGGCGTCCCAGCGC
GCGGCGGGCGCGTCGGGCGGCGTTACGGTCGGCGTTGGCGTCGGCACCGAACAGCGCA
ACCTGAGCGTCGTGGCCCCGTCGCAGTTCACGTTCTCGTCCCGCTCGCCGGATTTCGTCGA
TGAAACGGCGGGCCAGTCGTGGTGCGCGATCCTCGGCCTTAATCAGTTCCATAGATCTTGA
TCTAGA

Figure 13C

I. trcD-Ag85B Brucella codon optimized: SEQ ID NO:4

```
   1 GTCGACCAGA AAAAGATCA AAAAAATTTG ACAATTAATC ATCCGGCTCG TATAATGTGT
  61 GGAATTGTGA GCGGATAACA ATTCACACA GGAAACAGCG CCGCTGAGAA AAGCGAAGC
 121 GGCACTGCTC TTTAACAATT TATCAGACAA TCTGTGTGGG CACTCGACCG GAATTATCGA
 181 TTAACTTTAT TATTAAAAAT TAAAGAGGTA TATATTAAATG TATCGATTAA ATAAGGAGGA
 241 ATAAACCATG CATCATCATC ATCATCATGG CCCCGCCTTC TCCCCGCCGG GCCTCCCGGT
 301 CGAATATCTC CAGGTTCCGT CCCCGAGCAT GGGCCGCGAC ATCAAGGTCC AGTTCCAGTC
 361 CGGCGGCAAC AATTCGCCGG CCGTCTATCT GCTTGACGGC CTTCGCGCGC AGGATGACTA
 421 TAATGGCTGG GATATCAACA CCCCGGCCTT CGAATGGTAT TATCAGAGCG GCCTGTCCAT
 481 CGTCATGCCG GTGGGCGGCC AGTCGAGCTT CTATTCGGAC TGGTATAGCC CGGCCTGCGG
 541 CAAGGCGGGC TGCCAGACCT ATAAGTGGGA AACCCTCCTG ACGTCGGAAC TCCCGCAGTG
 601 GCTGAGCGCC AATCGCGCGG TGAAGCCGAC GGGCTCCCGC GCGATCGGCC TCTCGATGGC
 661 CGGCTCCTCG GCGATGATCC TGGCCGCGTA TCATCCGCAG CAGTTCATCT ATGCCGGCTC
 721 CCTGTCGGCG CTTCTCGACC CGAGCCAGGG CATGGGCCCG TCCCTGATCG GCCTTGCCAT
 781 GGGCGATGCG GGCGGCTATA AGGCCGCGGA TATGTGGGGC CCGAGCTCCG ACCCGGCCTG
 841 GGAACGCAAC GATCCGACCC AGCAGATCCC GAAGCTTGTT GCCAACAATA CCCGCCTCTG
 901 GGTCTATTGC GGCAACGGCA CGCCGAATGA ACTGGGCGGC GCCAATATCC CGGCGGAATT
 961 CCTGGAAAAT TTCGTGCGCT CGAGCAACCT TAAGTTCCAG GATGCCTATA ACGCCGCGGG
1021 CGGCCATAAC GCGGTTTTCA ATTTCCCGCC GAACGGCACG CACTCGTGGG AATATTGGGG
1081 CGCGCAGCTC AATGCCATGA AGGGCGACCT CCAGTCCTCC CTCGGGCGCG GCAGATCTTA
1141 ATCTAGA
```

Figure 14A

```
trcD-Ag85B with matched amino acids: SE

II. trcD-Rv2660C::ESAT6 Brucella codon optimized: SEQ ID NO: 6

```
  1 GTCGACCAGA AAAAGATCA AAAAATTTG ACAATTAATC ATCCGGCTCG TATAATGTGT
 61 GGAATTGTGA GCGGATAACA ATTTCACACA GGAAACAGCG CCGCTGAGAA AAAGCGAAGC
121 GGCACTGCTC TTTAACAATT TATCAGACAA TCTGTGTGGG CACTCGACCG GAATTATCGA
181 TTAACTTTAT TATTAAAAAT TAAAGAGGTA TATATTAATG TATCGATTAA ATAAGGAGGA
241 ATAAACCATG CATCATCATC ATCATCATGG TGGATCCGTT ATCGCGGGCG TCGATCAGGC
301 GCTTGCGGCC ACGGGCCAGG CGTCCCAGCG CGCGGCCAGG GCGTCGGGCG GCGTTACGGT
361 CGGCGTTGGC GTCGGCACCG AACAGCGCAA CCTGAGCGTC GTGGCCCCGT CGCAGTTCAC
421 GTTCTCGTCC CGCTCGCCGG ATTTCGTCGA TGAAAACGGG GGCCAGTCGT GGTGCGCGAT
481 CCTCGGCCTT AATCAGTTCC ATAGATCCAT GACGGAACAG CAGTGGAATT TCGCCGGCAT
541 CGAAGCCGCC GCCTCCGCCA TCCAGGGCAA TGTGACGAGC ATCCATAGCC TCCTCGATGA
601 AGGCAAGCAG TCGCTGACCA AGCTTGCCGC GGCCTGGGGC GGCTCGGGCA GCGAAGCGTA
661 TCAGGGCGTC CAGCAGAAGT GGGACGCGAC CGCCACCGAA CTTAACAATG CGCTCCAGAA
721 CCTGGCCCGC ACGATCTCGG AAGCGGGCCA GGCGATGGCG TCCACGGAAG GCAATGTCAC
781 GGGCATGTTC GCGAGATCTT AATCTAGA
```

*Figure 14C* trcD-Rv2660C::ESAT6 with matched amino acids: SEQ ID NO:7

```
     M  H  H  H  H  H  H  G  G  S  V  I  A  G  V  D  Q  A  L  A
  1  atgcatcatcatcatcatcatggtggatccgttatcgcgggcgtcgatcaggcgcttgcg   60
     A  T  G  Q  A  S  Q  R  A  A  G  A  S  G  G  V  T  V  G  V
 61  gccacgggccaggcgtccagcagcgcgcggcggcaggcagcagcggcgtcacggtcggtgtt  120
     G  V  G  T  E  Q  R  N  L  S  V  V  A  P  S  Q  F  T  F  S
121  ggcgtcggcaccgaacagcgcaacctgagcgtcgtggccccgtcgcagttcacgttctcg  180
     S  R  S  P  D  F  V  D  E  T  A  G  Q  S  W  C  A  I  L  G
181  tcccgctcgccggatttcgtcgatgaaacgcggcaagtcgtggtgcgatcctcggc  240
     L  N  Q  F  H  R  S  M  T  E  Q  W  N  F  A  G  I  E  A
241  cttaatcagttccatcgatccatgacgggaacagcagtgaatttcgccggcatcgaagcc  300
     A  A  S  A  I  Q  G  N  V  T  S  I  H  S  L  L  D  E  G  K
301  gccgcctccgcgcatcagggcaatgtgacgagcatccatagcctcctcgatgaaggcaag  360
     Q  S  L  T  K  L  A  A  A  W  G  G  S  G  S  E  A  Y  Q  G
361  cagtcgctgaccaagcttgccgcgcggtggcctgggcagcgaagcgtatcaggc  420
     V  Q  Q  K  W  D  A  T  A  T  E  L  N  N  A  L  Q  N  L  A
421  gtccagcagaagtgggacgcgaccgccacggaacttaacaatgcgctccagaacctggcc  480
     R  T  I  S  E  A  G  Q  A  M  A  S  T  E  G  N  V  T  G  M
481  cgcacgatctcggaagcgcaggcgatggcgtccacggaaggcaatgtcacgggcatg  540
     F  A  R  S  *  S  R
541  ttcgcgagatcttaatctaga  561
```

Figure 14D

Amino acid Sequence of Protein Product 6X His-tag-Ag85B: SEQ ID NO: 8

Met H H H H H H G G S E S R P G L P V E Y L Q V P S P S Met G R D I K V Q F Q S G G N
N S P A V Y L L D G L R A Q D D Y N G W D I N T P A F E W Y Y Q S G L S I V Met P V G
G Q S S F Y S D W Y S P A C G K A G C Q T Y K W E T L L T S E L P Q W L S A N R A V K
P T G S A A I G L S Met A G S S A Met I L A A Y H P Q Q F I Y A G S L S A L L D P S Q
G Met G P S L I G L A Met G D A G G Y K A A D Met W G P S S D P A W E R N D P T Q Q I
P K L V A N N T R L W V Y C G N G T P N E L G G A N I P A E F L E N F V R S S N L K F
Q D A Y N A A G G H N A V F N F P P N G T H S W E Y W G A Q L N A Met K G D L Q S S L
G A G R S Stop Met H H H H H H G G S = 6x His-tag
E = start of Ag85B

*Figure 14E*

Amino acid Sequence of Protein Product 6X His-tag-Rv2660c::ESAT6: SEQ ID NO: 9

Met H H H H H H G G S V I A G V D Q A L A A T G Q A S Q R A A G A S G G V T V G G V
G T F Q R N L S V V A P S Q F T F S S R S P D F V D E T A G Q S W C A I L G L N Q F H
R S Met T E Q Q W N F A G I E A A A S A I Q G N V T S I H S L L D E G K Q S L T K L A
A W G G S G S E A Y Q G V Q Q K W D A T A T E L N N A L Q N L A R T I S E A G Q A
Met A S T E G N V T G Met F A R S Stop Met H H H H H H G G S - 6x His-tag
V - Start of Rv2660c
Met - Start of ESAT6

*Figure 14F*

MULTIVALENT *BRUCELLA* VACCINE FOR PROTECTION AGAINST MYCOBACTERIAL INFECTIONS AND METHODS OF USING THE SAME

FIELD OF THE INVENTION

The invention generally relates to recombinant *Brucella* strains as vaccines and methods of administering the same for *Brucella* and mycobacterial infections in mammals. For example, the invention provides a leucine auxotrophic strain RB51leuB as an attenuated vaccine able to express at least one of the *Mycobacterium tuberculosis* protective antigens Ag85B, RV2660c and ESAT6.

PRIORITY

This application claims the benefit of U.S. application 62/047,945, filed Sep. 9, 2014. This application is incorporated herein by reference in its entirety.

SEQUENCE LISTING

This document incorporates by reference an electronic sequence listing text file, which was electronically submitted along with this document. The text file is named 01640672 ST25.txt, is 14.4 kilobytes, and was created on Sep. 8, 2015.

BACKGROUND OF THE INVENTION

Brucellosis is an infectious disease caused by bacteria of the genus *Brucella*. There are various *Brucella* species that are capable of infecting both wildlife and livestock. The principal cause of brucellosis in cattle is the bacterium *B. abortus*. Infected cattle commonly have high incidences of spontaneous abortions, arthritic joints, and retained placenta following calving. In the United States, infected cows are often killed. Sheep and goats are the preferred hosts of *B. melitensis*, which is the *Brucella* species most virulent for humans. Humans can become infected by coming in contact with infected animals or animal products, such as unpasteurized milk, that are contaminated with these bacteria.

Vaccines are used to protect against diseases, which are caused by pathogens. These pathogens are microbial organisms, such as bacteria and viruses, which affect animals, including humans. Vaccines are primarily derived from a pathogen by producing and administering either: a) an attenuated or avirulent version of the pathogen; b) the killed pathogen; c) extracted protective antigens or antigen mixes of the pathogen (homologous antigens); or d) a microorganism expressing one or more protective antigens encoded by cloned genes originating in a microbial pathogen different from the vaccine strain (heterologous antigens).

Vaccines for both bacteria and viruses are engineered from microorganisms expressing one or more protective antigens, as described by K. Jones and M. Sheppard in Designer Vaccines, CRC Press (1997). Vaccines are intended to produce an immune response in the recipient consisting of at least one of an antibody mediated or T cell mediated immune response, thereby preventing future infection by a pathogen, or fighting a current pathogenic infection. In particular, vaccines against facultative intracellular pathogens, those growing inside the cells of the infected host, need to induce a strong and appropriate cell mediated immune response. In contrast, vaccines against obligate extracellular pathogens need to induce an appropriate antibody mediated immune response. Often, regardless of the pathogen, an appropriate combined antibody and cellular mediated immune response leads to sufficient protection or relief from infection. In order to achieve this protection or relief from infection, vaccines may express one or more homologous antigens, heterologous antigens, or a combination of both.

Vaccines may be administered to vertebrates both to prevent and treat infection by pathogens. Thus, vaccines are frequently administered to prevent the spread of a disease caused by a pathogen. In particular, herd animals, such as cows, goats, sheep and swine, are often vaccinated to prevent the spread of a disease among members of the herd. Further, because certain diseases may travel between vertebrates, including travel between various animals and between animals and humans, vaccines are used to prevent the spread of disease between various species, usually by administration to the infected animal and other uninfected animals in the immediate vicinity. However, other animals in the area which are less likely to contract the disease may also be vaccinated as a prophylactic measure. For example, an infected cow and its as yet uninfected herd may be vaccinated to treat a disease and prevent its further spread. As a prophylactic measure, other animals which are likely to contract the disease from the infected cow, such as neighboring cows, sheep or humans, may be vaccinated as well.

*B. abortus* strain RB51 is a stable rough mutant derived from the wild-type virulent strain *B. abortus* 2308 [1]. This strain is currently the official USDA approved vaccine against cattle brucellosis in the United States and elsewhere. The safety and protective efficacy of strain RB51 have been well demonstrated under laboratory and field conditions [2, 3]. Protection afforded by strain RB51 vaccination is due to induction of cell-mediated immune mechanisms including antigen-specific induction of IFN-γ production [4-6]. Multiple studies have exploited the advantageous vaccinal qualities of strain RB51 as a host for the delivery of protective antigens of other intracellular pathogens in which a Th1 type immune response or cell-mediated immunity is essential for protection [7, 8].

Previously, plasmid-based expression systems have been utilized to express heterologous proteins in strain RB51 [5, 8-13]. However, these expression vectors usually encode antibiotic resistance markers. Moreover, the U.S. Food and Drug Administration strongly discourages and strictly regulates the introduction of antibiotic resistance genes into live attenuated vaccines [14]. In addition, often such expression systems are unstable in the absence of antibiotic selection pressure. To overcome this hurdle, an environmentally safe leucine auxotroph strain of RB51 (RB51leuB) was created to over-express foreign antigens without using antibiotic resistance marked plasmids [15]. The production of this strain is described in US 2010/0226942 herein incorporated by reference. This auxotrophic strain can be complemented with the pNS4 vector expressing the wild-type leuB gene. This complementation allows for survival of the strain in leucine-deficient minimal medium and under nutrient-limiting conditions in vivo, thus providing selective pressure for plasmid maintenance without using antibiotic selection markers [16].

Although the creation of the strain RB51leuB and pNS4 has led to a safer and more stable platform for expression of other foreign antigens, additional modifications are necessary to allow for better and more consistent expression in this host-vector system. Additionally, a need remains in the art for immunogenic compositions and multivalent vaccines to combat *Brucella* and other bacterial infections such as those caused by mycobacteria. Similar to *Brucella*, humans can become infected with *M. tuberculosis* by coming in contact with infected animals or animal products, such as unpasteurized milk, that are contaminated with these bacteria. Additionally, the available *Brucella* vaccines can be effective in controlling brucellosis, but they can have numerous drawbacks, such as interference with diagnostic tests, pathogenicity for humans, and potential to cause abortion in pregnant animals.

SUMMARY OF THE INVENTION

One aspect of the invention provides a multivalent *Brucella* vaccine strain expressing at least one heterologous *Mycobacterium* antigen. In exemplary embodiments, the *Mycobacterium* is *M. tuberculosis*. In some embodiments, the vaccine improves upon the RB51leuB and pNS4 platform such that the transcriptional activity of genes carried on this plasmid is strengthened by utilizing a stronger promoter and the codon usage is modified to that of *Brucella*. These modifications to pNS4 allow for better expression of antigens of other intracellular pathogens in which cell-mediated immunity is essential for protection e.g. *M. tuberculosis*. The vaccines described herein serve as an environmentally safe bivalent vaccine for protection against *Brucella* and *Mycobacterium* infections simultaneously.

An embodiment of the invention provides a multivalent vaccine or immunogenic composition comprising at least one *Brucella* strain transformed with a vector expressing at least one *Mycobacterium* antigen, wherein said at least one *Mycobacterium* antigen is codon optimized for expression in said at least one *Brucella* strain and a vehicle or carrier suitable for administration to a subject. In exemplary embodiments, the *Brucella* strain is *B. abortus* strain RB51leuB and the *Mycobacterium* antigen is a *M. tuberculosis* antigen. In some embodiments, the *M. tuberculosis* antigen is selected from the group consisting of Ag85B, Rv2660c, and ESAT6. The antigens Rv2660c and ESAT6 can expressed as a fusion protein. In exemplary embodiments, the vaccine or immunogenic composition includes a first *Brucella* strain that is transformed with a vector expressing Ag85B and a second *Brucella* strain that is transformed with a vector expressing Rv2660c and ESAT6. In preferred embodiments, the *M. tuberculosis* antigen is codon optimized for the at least one *Brucella* strain.

Another aspect of the invention provides a chimeric *Brucella* strain and one or more sequences coding for at least one *Mycobacterium* antigen wherein said at least one *Mycobacterium* antigen is codon optimized for expression in said *Brucella*. In some embodiments, the *Brucella* is *B. abortus* strain RB51leuB. In exemplary embodiments, the chimeric *Brucella* strain is XXXX, having NRRL accession number YYY-1111 Additional embodiments of the invention provide a pNS4leuB plasmid comprising one or more sequences of heterologous *Mycobacterium* antigens.

An additional aspect of the invention relates to a method for protecting or treating a subject at risk of or suffering from at least one disease caused by one or more bacterium, said method comprising administering to the subject an effective amount of a vaccine or immunogenic composition according to the invention. In some embodiments, the method further comprises the step of administering at least one purified polypeptide comprising at least one of Ag85B, Rv2660c, and ESAT6 as a booster to the vaccine. In exemplary embodiments, the subject is administered a first purified polypeptide comprising Ag84B and a second purified polypeptide comprising ESAT6. In some embodiments, a live vaccine is first administered and then the vaccination can be boosted with purified polypeptide antigens or another dose of the engineered RB51leuB expressing the Mycobacterial antigens. The disease can be brucellosis and/or tuberculosis and the bacterium can be *B. abortus* and/or *M. tuberculosis*. In some embodiments, the subject is selected from the group consisting of humans, cows, sheep, goats, pigs, bison, elk, and camels. In exemplary embodiments, the animal is a cow.

A further aspect of the invention provides a method of raising an immune response to both *Mycobacterium* and *Brucella* in a subject, said method comprising the step of administering to the subject a chimeric *Brucella* as described herein. In some embodiments, the method further comprises a step of administering to said subject a booster a period of time after said administering step, said booster including one or more *Mycobacterium* antigens or one or more nucleotides coding for said one or more *Mycobacterium* antigens.

BRIEF DESCRIPTION OF THE DRAWINGS

FIG. 4A-C. ELISA detection of ESAT6-specific IgG (A), IgG2a (B) and IgG1 (C) antibodies in serum of mice vaccinated with strain RB51leuB, RB51-Rv2660c::ESAT6, RB51FlgE-Rv2660c::ESAT6 or inoculated with saline alone. Sera collected from three mice of each group at 3 and 6 weeks post-vaccination were diluted 1:50 and assayed for the presence of specific antibodies. Results were shown as the means±S.D of $OD_{450}$ of the color developed.

FIG. 13A-C. *M. tuberculosis* Nucleic acid sequences of A) ESAT6, B) Ag85B, and C) Rv2660c modified as per *Brucella* codon usage.

FIG. 14A-F. Nucleic acid and amino acid sequences of a portion of the pNS4 plasmid encoding codon-optimized Ag85B (A, B; SEQ ID NO: 4-5) and Rv2660C::ESAT6 (C, D; SEQ ID NO: 6-7) downstream of a TrcD promoter. (E) Amino acid Sequence of Protein Product 6× His-tag-Ag85B; SEQ ID NO: 8. (F) Amino acid Sequence of Protein Product 6× His-tag-RV2660c::EAST6; SEQ ID NO: 9.

DETAILED DESCRIPTION

Figure 1:
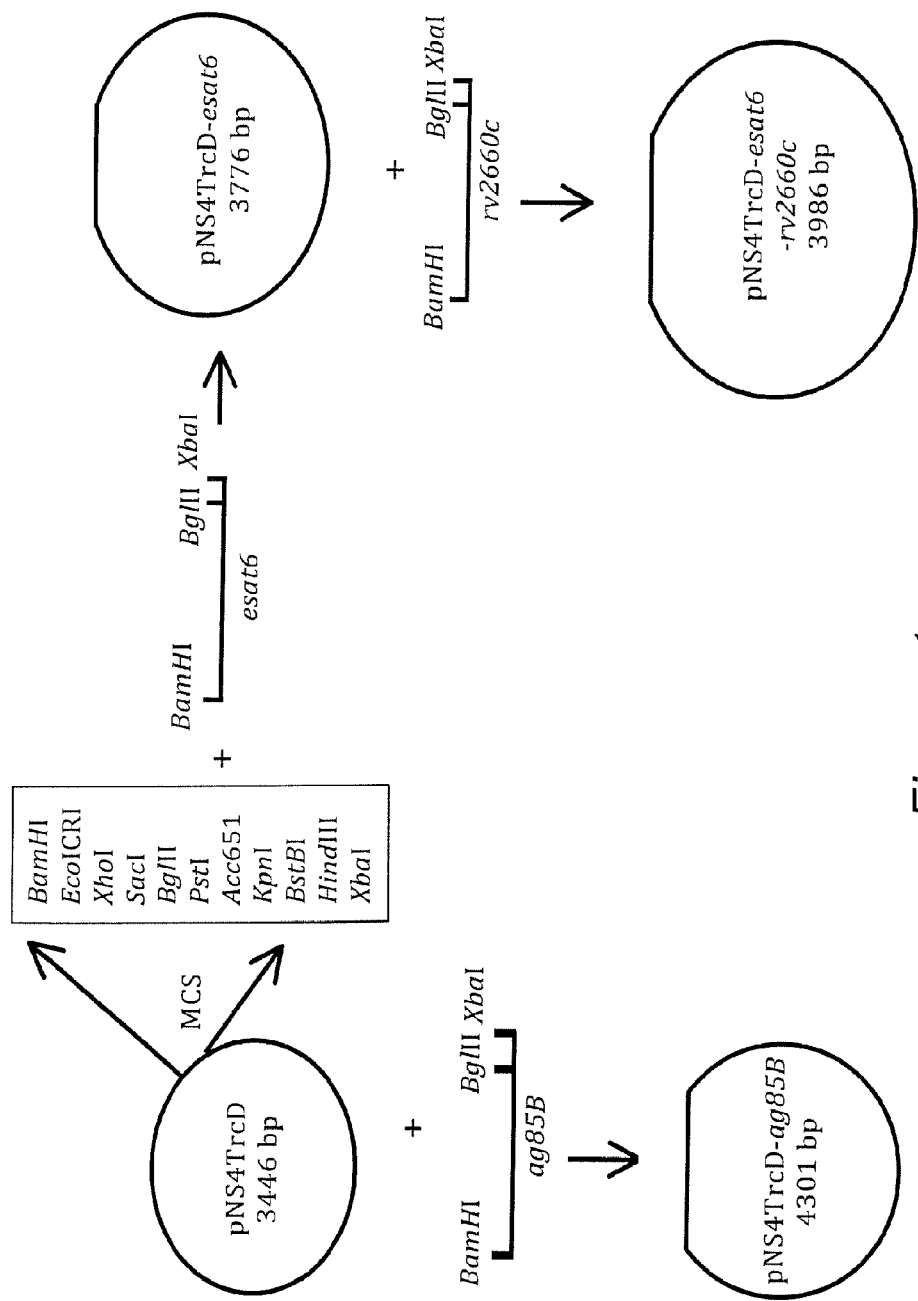
FIG. 1. Diagram depicting the cloning strategy for construction of the expression vectors carrying synthetic mycobacterial genes. ag85B was cloned into pNS4TrcD via BamHI and XbaI restriction sites. rv2660c was cloned into pNS4TrcD via BamHI and XbaI restriction sites. esat6 was cloned into pNS4TrcD-rv2660c via BglII and XbaI restriction sites.

One aspect of the invention provides vaccines and immunogenic compositions that, when administered to a subject, elicit an immune response to *Brucella* and *Mycobacterium* in the subject, e.g. a protective immune response. Methods for using the immunogenic compositions/vaccines to prevent or attenuate the spread of *Brucella* and *M. tuberculosis* infection in susceptible individuals and in groups of susceptible individuals are also provided. In some embodiments, the expression of mycobacterial antigens does not alter the efficacy of the *Brucella* vaccine strain. In further embodiments, a vaccine as provided herein will not turn the subject diagnostically positive to a tuberculin skin test.

The vaccines provided herein can be in the form of recombinant polypeptides involved in evoking an immune response to bacterium of the genus *Brucella* and/or *Mycobacterium*, nucleic acid vectors (e.g., plasmids) designed to express such recombinant polypeptides, and bacteria transformed with such nucleic acids. The vaccines provided herein can be used to immunize or treat any type of animal including, without limitation, cows, sheep, goats, pigs, bison, elk, camels, dogs, poultry or any vertebrate species that contracts brucellosis and/or tuberculosis, such as humans.

The vaccines provided herein can be used to induce an immune response against any species of *Brucella* including, without limitation, *B. abortus, B. canis, B melitensis, B. neotaomae, B. ovis, B. suis* and *B. pinnipediae*. For example, a vaccine provided herein can protect against more than one species of *Brucella*. In some cases the vaccines provided by this invention can be used to induce an immune response against a pathogen that causes spontaneous abortion in cattle (e.g., *Neospora caninum*). The vaccines provided can be used to reduce the risk of developing symptoms associated with the disease known as brucellosis.

The vaccines provided herein can be used to induce an immune response against any species of *Mycobacterium* including, without limitation, *M. tuberculosis, M. bovis, M. africanum, M. canetti*, and *M. caprae*.

One aspect of the invention relates to methods of administering a vaccine as described herein. The methods involve administering an effective amount of a vaccine, where the effective amount is sufficient to prevent the development of or lessen the extent of the development of symptoms of a *Brucella* and/or *Mycobacterium* infection in the subject, when the subject is later exposed to the bacterium or contracts a bacterial infection.

Embodiments of this invention also provide methods and materials relating to isolated nucleic acid molecules, substantially pure polypeptides, and bacteria that contain an isolated nucleic acid molecule. The term "nucleic acid" as used herein encompasses both RNA and DNA, including cDNA, genomic DNA, and synthetic (e.g., chemically synthesized) DNA. The nucleic acid can be double-stranded or single stranded. Where single-stranded, the nucleic acid can be the sense strand or the antisense strand. In addition, nucleic acid can be circular or linear. The term "isolated" as used herein with reference to nucleic acid refers to a naturally-occurring nucleic acid that is not immediately contiguous with both of the sequences with which it is immediately contiguous (one of the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retro virus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus) or the genomic DNA of a prokaryote or eukaryote. In addition, a non-naturally-occurring nucleic acid can include a nucleic acid molecule that is part of a hybrid or fusion nucleic acid sequence. It will be apparent to those of ordinary skill in the art that a nucleic acid existing among hundreds to millions of other nucleic acid molecules within, for example, cDNA or genomic libraries, or gel slices containing a genomic DNA restriction digest is not to be considered an isolated nucleic acid.

The terms "peptide", "polypeptide" and "protein" may be used interchangeably herein. Chimeric or fusion peptide or polypeptide refers to a recombinant or synthetic peptide or polypeptide whose primary sequence comprises two or more linear amino acid sequences which do not both occur in a single molecule in nature, or at least are not linearly contiguous in a single molecule in nature. (For example, they may both be present in a single molecule which comprises e.g. amino acids 1-15, but in the fusion or chimera, "amino acids 1-5" and amino acids 10-15" are present but amino acids 6-9 are not present between the sequence represented by amino acids 1-5 and the sequence represented by amino acids 10-15.) The two or more sequences may be, for example, a peptide (e.g. an epitope or antigenic region) and a linker sequence, or two or more peptides (which may be the same or different) which are either contiguous or separated by a linker sequence, etc.

A polypeptide as described herein can be an antigen that produces an immune response in an animal (e.g., antibody production). In some cases a polypeptide provided herein can be expressed as a homologous or heterologous antigen. For example a polypeptide can be an antigen, which is recognized as foreign when expressed in an animal, or a polypeptide can be an enzyme that produces an antigen, which is recognized as foreign when expressed in an animal. For example, a polypeptide provided herein can be an antigen that produces an immune response against *Brucella* (e.g., a ribosomal protein, an outer membrane protein, a periplasmic protein, or a lipopolysaccharide isolated from a species of *Brucella*). In some cases, a polypeptide can produce an immune response effective against one species of *Brucella* and another polypeptide can produce an immune response effective against a different species of *Brucella* or against a species of a different bacterial genus such as *Mycobacterium*. For example, a polypeptide provided herein can be a heterologous antigen that produces an immune response against *M. tuberculosis*, such as ESAT6 (GenBank accession number DQ451152.1), Ag85B (GenBank accession number AY207396), and Rv2660c (NCBI Reference Sequence: NC_000962.3). In exemplary embodiments, the heterologous antigens are codon-optimized for expression in the *Brucella* strain. For example, the ESAT6, Ag85B, and Rv2660c antigens codon-optimized for expression in RB51leuB are represented by SEQ ID NO: 1, SEQ ID NO: 2, and SEQ ID NO: 3, respectively (see FIG. 13A-C). Ag85B and ESAT6 are secreted antigens of *M. tuberculosis* having a size of about 31 kDa and 10 kDa, respectively. Rv2660c is an *M. tuberculosis* antigen of about 10 kDa. In some embodiments, the polypeptide includes a fusion of two or more antigens. Any Mycobacterial antigen or antigenic fragment may be used in the compositions and methods of the invention including, but not limited to, the antigens disclosed in US20130345079 and U.S. Pat. No. 6,991,797, herein incorporated by reference. Protective antigens from bacteria, viruses parasites, or fungi may be used in the compositions and methods of the invention.

Antigen is a term used historically to designate an entity that is bound by an antibody, and also to designate the entity that induces the production of the antibody. More current usage limits the meaning of antigen to that entity bound by an antibody, while the word "immunogen" is used for the entity that induces antibody production. Where an entity discussed herein is both immunogenic and antigenic, reference to it as either an immunogen or antigen will typically be made according to its intended utility. The terms "antigen", "antigenic region" "immunogen" and "epitope" may be used interchangeably herein. As used herein, an antigen, immunogen or epitope is generally a portion of a protein (e.g. a peptide or polypeptide).

In some embodiments, a vaccine provided herein can be delivered as a prophylactic vaccine to reduce the risk of developing brucellosis should a *Brucella* infection occur. In some cases, a vaccine provided herein can reduce the risk of developing brucellosis from infection by *B. abortus, B. canis, B. melitensis, B. neotomae, B. ovis, B. suis* or *B. pinnepediae* bacteria. A vaccine provided herein can also be delivered as a prophylactic vaccine to reduce the risk of developing tuberculosis should a *M. tuberculosis* infection occur.

Another aspect of this invention provides methods for preparing a vaccine provided herein. Such methods can include transforming bacteria with an amount of a nucleic acid vector (e.g., plasmid). Transformation can be achieved by any appropriate method, including, for example, electroporation or chemical transformation. A vaccine can be produced using an isolated nucleic acid to transform a bacterial culture. For example, a transformed bacterial culture can over-express antigens to produce an immune response. In some cases an isolated nucleic acid provided herein can include a nucleic acid encoding one or more than one (a plurality) of antigens. For example, an isolated nucleic acid can encode one or more of an Ag85B, ESAT6, and/or Rv2660c polypeptide. As a further example, an ESAT6 polypeptide and an Rv2660c polypeptide may be encoded. Therefore, in some cases the vaccines disclosed herein can include one or more nucleic acids that encode, for example, two, three, or four (or more) polypeptides.

In some cases, a vaccine provided herein can include a marker of delivery and expression. For example, a vaccine can include a nucleic acid that encodes a fluorescent polypeptide (e.g., a green fluorescent protein, GFP) as a marker of expression and delivery of the vaccine to an animal. For example, a marker of delivery and expression can be detected e.g. as antibodies to the marker. For example, GFP antibodies may be detected in sera from immunized animals.

Some embodiments of the invention relate to an isolated pNS4leuB plasmid comprising one or more Mycobacterial antigen sequences, such as one or more sequences selected from the group consisting of SEQ ID NO: 1, SEQ ID NO: 2, and SEQ ID NO: 3. In exemplary embodiments, the pNS4leuB plasmid contains a sequence selected from the group consisting of SEQ ID NO:4-7. Other exemplary plasmids include pNSch (GenBank accession number DQ412050) and pNSTrcD (GenBank accession number DQ412056). Exemplary sequences of protein products produced from said plasmins include SEQ ID NO: 8 and SEQ ID NO:9. In some cases, an isolated nucleic acid provided herein can include a promoter for driving expression of a polypeptide. For example, an isolated nucleic acid can include a nucleic acid encoding a polypeptide operably linked to a promoter sequence.

A nucleic acid as provided herein may comprise at least one "core" sequence or segment consisting of a sequence from one or more of Ag85B, ESAT6, and Rv2660c. In such constructs, which can be chimeric or fusion polypeptides or proteins, the core sequence(s) is/are flanked on at least one of the amino terminus and carboxy terminus (i.e. at one or the other or both termini) by a sequence which is not found adjacent to the core sequence in nature. The sequence which is not found adjacent to the core sequence in nature may be a heterologous sequence (e.g. synthetic and/or from another species or strain) or may be a repeat or duplication of the same sequence. In some constructs, one core sequence is present alone; in other constructs, multiple core sequences of a single type (i.e. Ag85B, ESAT6, or Rv2660c) are present. In yet other constructs, one core sequence from at least two of Ag85B, ESAT6, and Rv2660c are present. In yet other constructions, multiple copies of one or more core sequence from at least two of Ag85B, ESAT6, and Rv2660c are present. For example, a single recombinant polypeptide may comprise one copy, or more than one copy (a plurality, two or more) of each of these different sequences. A single polypeptide may contain two or more copies of a single sequence, a single copy of one sequence and two or more copies of one or more different sequences, or two or more copies of at least two different sequences. Another aspect of the disclosure provides a mixture of at least two of any of the peptides and/or polypeptides described herein.

It is contemplated that virtually any protein sequence, as well as its corresponding nucleic acid sequence coding for the protein sequence that is or includes Ag85B, ESAT6, or Rv2660c may be used as described herein. This includes the full length sequence as well as any sequence of, for example from about 5-50 (or less than 5 or more than 50) amino acids at the beginning (amino terminus) or at the end (carboxy terminus) of the amino acid sequence of Ag85B, ESAT6, or Rv2660c. The polypeptide sequences as described herein may also be shortened on either the amino or carboxy terminus (or both) by one, two, or more amino acids to produce fragments within the context of the invention wherein the fragments produce the same or a similar protective effect. Alternatively, the polypeptide may be a chimera or fusion protein which comprises flanking amino acids sequences which are not adjacent to the native sequence in nature. For example, the adjacent sequences may be corresponding amino acids which are from different but related species; or amino acids which are from different species (e.g. from other bacteria or eukaryotes of interest, e.g. from infectious agents); or from a synthetic sequence, e.g. various tags such as histidine or glutathione S-transferase (GST) tags, linkers, spacers, targeting sequences, etc.).

A nucleic acid encoding an antigen such as Ag85B can be operably linked to a TrcD promoter sequence (e.g. FIG. 1). In some cases, an isolated nucleic acid can be transcribed in more than one direction. For example, transcription of a nucleic acid encoding an Ag85B polypeptide can proceed in a clockwise direction and transcription of a nucleic acid encoding a GFP polypeptide can proceed in a counterclockwise direction.

In addition to polypeptide sequences from *M. tuberculosis* antigens, other sequences may be included in the polypeptides of the invention. Such sequences include but are not limited to: antigenic peptide sequences such as linker sequences which in and of themselves can be antigenic and/or various sequences which serve as markers of delivery and expression, as discussed above. Examples of recombinant protein tags that may be useful in practicing the invention include but are not limited to glutathione-S-transferease (GST), poly-histidine, maltose binding protein (MBP), FLAG, V5, halo, myc, hemaglutinin (HA), S-tag, calmodulin, tag, streptavidin binding protein (SBP), SoftagI™, Softag3™, Xpress tag, isopeptag, Spy Tag, biotin carboxyl carrier protein (BCCP), GFP, Nus-tag, strep-tag, thioredoxin tag, TC tag, and Ty tag. Examples of linker sequences include but are not limited to an amino acid spacer, an amino acid linker, a signal sequence, a stop transfer sequence, a transmembrane domain, and a protein purification ligand. It should also be recognized that a multitude of other such sequences are known to those of skill in the art, and inclusion of other antigenic, linker, or tag sequences is contemplated.

In some embodiments of the invention, individual linear epitopes in a chimeric vaccinogen are separated from one another by intervening sequences that are more or less neutral in character, i.e. they do not in and of themselves elicit an immune response to Mycobacteriaceae. Such sequences may or may not be present between the epitopes of a chimera. If present, they may, for example, serve to separate the epitopes and contribute to the steric isolation of the epitopes from each other. Alternatively, such sequences may be simply artifacts of recombinant processing procedures, e.g. cloning procedures. Such sequences are typically known as linker or spacer peptides, many examples of which are known to those of skill in the art. See, for example, Crasto, C. J. and J. A. Feng. 2000.

Those of skill in the art will recognize that, while in some embodiments of the invention, the amino acid sequences that are chosen for inclusion in the polypeptides of the invention correspond exactly to the primary amino acid sequence of the original or native sequences of an Ag85B, ESAT6, or Rv2660c protein, this need not always be the case. The amino acid sequence of an epitope that is included in the polypeptides of the invention may be altered somewhat and still be suitable for use in the present invention. For example, certain conservative amino acid substitutions may be made without having a deleterious effect on the ability of the polypeptides to elicit an immune response. Those of skill in the art will recognize the nature of such conservative substitutions, for example, substitution of a positively charged amino acid for another positively charged amino acid (e.g. K for R or vice versa); substitution of a negatively charged amino acid for another negatively charged amino acid (e.g. D for E or vice versa); substitution of a hydrophobic amino acid for another hydrophobic amino acid (e.g. substitution of A, V, L, I, W, etc. for one another); etc. All such substitutions or alterations of the sequences of the polypeptides that are disclosed herein are intended to be encompassed by the present invention, so long as the resulting polypeptides still function to elicit a suitable immune response. In addition, the amino acid sequences that are included in the polypeptides or any chimeric proteins of the invention need not encompass a full length native polypeptide. Those of skill in the art will recognize that truncated versions of amino acid sequences that are known to be or to contain antigenic polypeptides may, for a variety of reasons, be preferable for use in the practice of the invention, so long as the criteria set forth for an epitope is fulfilled by the sequence. Amino acid sequences that are so substituted or otherwise altered may be referred to herein as "based on" or "derived from" the original wild type or native sequence. In general, the Ag85B, ESAT6, or Rv2660c proteins or polypeptide fragments from which the linear epitopes are "derived" or on which the linear epitopes are "based" are the Ag85B, ESAT6, or Rv2660c proteins or peptide fragments as they occur in nature. These natural Ag85B, ESAT6, or Rv2660c proteins may alternatively be referred to as native or wild type proteins.

Such changes to the primary sequence may be introduced for any of a variety of reasons, for example, to eliminate or introduce a protease cleavage site, to increase or decrease solubility, to promote or discourage intra- or inter-molecular interactions such as folding, ionic interactions, salt bridges, etc., which might otherwise interfere with the presentation and accessibility of the individual epitopes along the length of a peptide or polypeptide. All such changes are intended to be encompassed by the present invention, so long as the resulting amino acid sequence functions to elicit a protective antibody response in a host to whom it is administered. In general, such substituted sequences will be at least about 50% identical to the corresponding sequence in the native protein, preferably about 60 to 70, or even 70 to 80, or 80 to 90% identical to the wild type sequence, and preferably at least about 95, 96, 97, 98, 99, or even 100% identical to a native Ag85B, ESAT6, or Rv2660c sequence or peptide fragment. The reference native Ag85B, ESAT6, or Rv2660c sequence or peptide fragment may be from any suitable type of Mycobacteriaceae, e.g. from any Mycobacteriaceae which is known to infect mammals.

A vaccine for producing an immune response against Brucella can be produced using any bacteria. For example, a bacterial strain such as B. abortus RB51 or RB51leuB can be used. The RB51leuB strain of bacterium exhibits leucine auxotrophy, having a mutation (i.e. deletion) at the leuB locus that disrupts expression of leuB (isopropyl malate dehydrogenase is necessary for leucine biosynthesis). In some embodiments, a leucine auxotrophic bacterial strain can be transformed with an isolated nucleic acid to restore leucine biosynthesis as described in US 2010/0226942, herein incorporated by reference.

The vaccines provided herein can be administered using any appropriate method. Administration can be, for example, topical (e.g. transdermal, ophthalmic or intranasal); pulmonary (e.g., by inhalation or insufflation or powders or aerosols); oral, or parenteral (e.g. by subcutaneous, intrathecal, intraventricular, intramuscular, or intraperitoneal injection, or by intravenous drip). Administration can be rapid (e.g., by injection) or can occur over a period of time (e.g., by slow infusion or administration of slow release formulations). In exemplary embodiments, the mode of administration is intraperitoneal. For application in livestock, the preferred mode of administration is subcutaneous or intramuscular.

In some embodiments, at least one booster vaccine, which may be a subunit booster vaccine, is administered after the initial administration of the vaccine of the invention. The booster vaccine may be identical to the vaccine that is initially used to vaccinate the subject Alternatively, the booster vaccine may be a subunit vaccine comprising isolated antigens or suitable antigenic fragments thereof, or nucleic acids encoding the protein or fragments, which are used to elicit an immunogenic response, e.g. a protective immunogenic response, in a subject. The booster vaccine may be administered between as early as four weeks after initial vaccination. In some embodiments, the booster vaccine may be administered one year or later after initial vaccination. In exemplary embodiments, the booster vaccine is administered between six weeks and 6 months after initial vaccination.

The immunogenic response from the initial or booster vaccine may protect a naive subject from subsequent full-blown Brucella and/or M. tuberculosis infection when exposed to the bacterium. Alternatively, administration of the initial or booster vaccine is used to provide treatment for an existing Brucella or M. tuberculosis infection, e.g. an active or latent TB infection. The protective response either wholly or partially prevents or arrests the development of symptoms related to disease or bacterial infection, in comparison to a non-vaccinated control organism, in which disease progression is not prevented.

The vaccines of the invention can include a pharmacologically suitable vehicle or carrier. The preparation of such compositions for use as vaccines is well known to those of skill in the art. Typically, such compositions are prepared either as liquid solutions or suspensions, however solid forms such as tablets, pills, powders and the like are also contemplated. The liquid may be an aqueous liquid. Solid forms suitable for solution in, or suspension in, liquids prior to administration may also be prepared. The preparation may also be emulsified. The active ingredients may be mixed with excipients, which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. The vaccine preparations of the present invention may further comprise an adjuvant, suitable examples of which include but are not limited to Seppic, Quil A, Alhydrogel, etc. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of polypeptides or chimeric peptides in the formulations may vary. However, in general, the amount in the formulations will be from about 0.01-99%, weight/volume.

In addition, the compositions may be administered in conjunction with other treatment modalities such as substances that boost the immune system, various anti-bacterial chemotherapeutic agents, antibiotics, and the like.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

Example 1. *Brucella abortus* Strain RB51 Expressing Mycobacterial Antigens Ag85B, Rv2660c-ESAT6 for Vaccination Against Mycobacterial and *Brucella* Infections Summary

*Brucella abortus* strain RB51 is the official USDA approved vaccine against cattle brucellosis in the United States and other countries. Protection conferred by strain RB51 vaccination is due to induction of cell-mediated immune mechanisms, including production of IFN-γ. In this study, the feasibility of using the leucine auxotrophic strain RB51leuB as an attenuated vaccine able to express *Mycobacterium tuberculosis* protective antigens (Ag85B, RV2660c and ESAT6) was evaluated. Two expression vectors were designed: pNS4TrcD-Ag85B, and pNS4TrcD-Rv2660c::ESAT6 (fusion construct). These vectors enabled strain RB51leuB to express the *M. tuberculosis* antigens Ag85B and fusion protein Rv2660c::ESAT6. In vivo and in vitro studies indicated that the recombinant vaccines were stable and continued to express the heterologous antigens in both selective and non-selective environments. The objective of this study was to develop and test the efficacy of the *B. abortus* vaccine strain RB51 as a platform for expression of *M. tuberculosis* antigens (Ag85B, ESAT6 and Rv2660c) and simultaneous induction of a protective immune response against *M. tuberculosis* and *B. abortus* challenge in mice.

The present studies show that expression of mycobacterial antigens in strain RB51leuB lead to strong induction of antigen-specific immune response characterized in this study by secretion of IgG2a antibodies as well as of IFN-γ and TNF-α. Mice immunized with an equal mix of two RB51leuB vaccines, one expressing fusion Rv2660c::ESAT6 and another expressing Ag85B led to borderline (p=0.052) protection against infection with *M. tuberculosis*. However, when mice were primed with these RB51leuB vaccines and boosted thereafter with proteins Ag85B and ESAT6, significant protection against a *M. tuberculosis* challenge was achieved and the protection level conferred was similar to that conferred by the *Bacillus* Calmette-Guerin (BCG) vaccine. Importantly, mice vaccinated with the RB51leuB vaccines did not become positive to the tuberculin skin test, indicating that they remained negative to the official diagnostic test for tuberculosis. Vaccination with purified Ag85B and ESAT6 engendered significant immunity but less than the protection engendered by the RB51leuB vaccines boosted with the purified antigens or BCG. The RB51leuB vaccine carrying the Rv2660c::ESAT6 antigens protected against infection against *Brucella abortus* as well as the RB51leuB vaccine. In conclusion, it was shown that recombinant RB51leuB strains expressing mycobacterial protective antigens result in stimulation of mycobacterial antigens specific immune responses without turning them positive in a tuberculosis infection diagnostic test. These vaccines can be used to prime animals for protection against *M. tuberculosis* infection and can simultaneously protect against *B. abortus* infection.

MATERIALS AND METHODS

Promoter Selection: Replacement of groE with trcD Promoter

The starting point for construction of the expression vectors was the pNS4GroE plasmid [13]. The groE promoter was excised from pNS4GroE expression plasmid with SalI and BamHI restriction enzymes and replaced with either trcD promoter [17] or a synthetic trcD promoter sequence to create the expression vector pNS4TrcD (FIG. 1).

Construction of Vectors Expressing Ag85B and Fusion Protein Rv2660c::ESAT6

The genes encoding *M. tuberculosis* protective antigens Ag85B, ESAT6 and Rv2660c (18) were optimized using *Brucella* codons and were commercially synthesized by Genscript (Piscataway, N.J., USA). *Brucella* codon optimization of these three protective antigens of *M. tuberculosis* has not been previously reported (see below). BamHI and XbaI restriction sites were engineered into the forward and reverse primers, respectively, to facilitate directional cloning into pNS4TrcD expression vector. A BglII restriction site was also designed in the reverse primers of Rv2660C, upstream of XbaI restriction site, for subsequent cloning of esat6 downstream of rv2660c. The amplified DNA regions (ag85B and rv2660c) were digested with BamHI and XbaI restriction enzymes and subcloned into the same sites of pNS4TrcD plasmid to generate pNS4TrcD-Ag85B and pNS4TrcD-Rv2660c, expression vectors (FIG. 1).

The construction of the Rv2660c::ESAT6 fusion vector was accomplished in two steps. In the first step, rv2660c was cloned as described earlier. In the second step, Esat6 gene containing BglII and XbaI restriction sites was amplified and then digested with BglII and XbaI restriction enzymes and subcloned into the same sites of pNS4TrcD-Rv2660c to generate pNS4TrcD-Rv2660c::ESAT6 expression chimeric vector (FIG. 1). Vectors pNS4TrcD-Ag85B and pNS4TrcD-Rv2660c::ESAT6 were then used through out this study and used to transform RB51leuB into RB51leuB-Ag85B and RB51leuB-Rv2660c::ESAT6 which are the vaccine strains used in this study (15).

pNS4: Was generated using the origin of replication and promoter of pNSGroE; details of pNSGroE as described in (http://www.ncbi.nlm.nih.gov/nuccore/49659742) The leuB gene of the strain RB51 along with its own promoter (1412 bp) was amplified by PCR using the primers (leuBForward, 5'GGG-AAG-CTT-GGG-TCT-AGA-AGT-TTC-GCT-CGC-GGT-GAG-TGG-CGA 3'3' SEQ ID NO:10 and leuBReverse, 5'GGG-ACT-AGT-TCA-GGC-CGA-AAG-TGC-CTT-GAA3' SEQ ID NO:11). The "origin of replication" (1700 bp) and 259 bp expression segment (*Brucella* groE promoter+multiple cloning site+6His tag) of the plasmid pNSGroE were amplified using the primers as described before as they have cloning sites as well as the minimal sequence necessary for plasmid replication (28); the groE promoter is up regulated following *Brucella* uptake into macrophages (31). After the restriction enzyme digestion, the 3 fragments were purified and ligated to form plasmid pNS4; note that this plasmid does not have an antibiotic resistance gene (FIG. 1). The leuB gene acts to complement any leuB *Brucella* auxotrophic strains carrying the plasmid under leucine limiting conditions i.e. minimal medium or inside the macrophage. (As described in *Brucella abortus* strain RB51 leucine auxotroph as an environmentally safe vaccine for plasmid maintenance and antigen overexpression. Rajasekaran P, Seleem M N, Contreras A, Purwantini E, Schurig G G, Sriranganathan N, Boyle S M. Appl Environ Microbiol. 2008 November; 74(22):7051-5. doi: 10.1128/AEM.01511-08. Epub 2008 Oct. 3.PMID: 18836016)

Details of the Constructs of the Two Protective Antigens from *Mycobacterium tuberculosis* for Expression in *Brucella abortus* RB51

The GroE promoter was replaced with TrcD promoter and the codons of the *M. tuberculosis* antigen were optimized for expression in *Brucella* species and cloned into pNS4 downstream of TrcD promoter. Expression of the *M. tuberculosis* antigens using our expression vector in strain RB51 was confirmed by western blotting.

Evaluation of Plasmid Stability In Vitro

To evaluate the stability of the two vectors expressing tuberculosis protective antigens, the gene for the green fluorescent protein (GFP) was cloned in-frame downstream of the mycobacterial genes. Strain RB51leuB was transformed with the GFP containing vectors and three random colonies containing each construct were subcultured onto agar made with either non-selective-enriched medium (TSA) or selective (leucine deficient) *Brucella* minimal medium (BMMleu). The subcultures were evaluated for GFP expression under UV light and, subsequently, subcultured onto BMMleu agar plates every 4 days until fluorescence was no longer observed.

Evaluation of Plasmid Stability in BALB/c Mice (In Vivo)

Five groups of 4-6 week old female BALB/c mice (n=9) were vaccinated with approximately $2-5 \times 10^8$ colony forming units (CFUs) of strain RB51leuB carrying one of following vectors pNS4TrcD-Rv2660c::ESAT6, pNS4TrcD-Ag85B, or pNS4TrcD (negative control). Three mice from each group were euthanized on weeks 3, 6, and 8 post-vaccination. Spleens and livers were aseptically harvested, homogenized, serially diluted and plated on TSA (non-selective medium) and BMMleu (selective medium) agar plates for CFU determination. The numbers of CFUs determined from growth on BMMleu were compared to the CFUs determined from growth on TSA to measure plasmid stability in vivo. Colonies isolated on BMMleu at week 6 were subject to western blotting for confirmation of protein expression i.e. mycobacterial antigens.

Preparation of the Protein Extract and Immunoblotting

Western blotting was performed on each recombinant strain using His tag antibodies to confirm expression and secretion of Ag85B and fusion protein Rv2660c::ESAT6. Briefly, cultures of strain RB51leuB carrying expression vectors were grown in BMMleu to mid-log phase. For cytoplasmic expression of Ag85B and the fusion protein Rv2660c-ESAT6, 100 ul of each culture was pelleted for 5 minutes in a micro centrifuge tube at 12,000×G. The pellet was lysed with β-mercaptoethanol in the presence of 10 mM Tris-base and heated in a water bath at 95° C. for 10 minutes. Western blot analysis was carried on proteins transferred onto nitrocellulose membranes and probed with 1:4000 dilutions of mouse IgG2a anti-His tag, horseradish peroxidase (HRP) conjugated sera (Life Sciences, Inc., Grand Island, N.Y., USA).

Mice:

Female BALB/c mice (6-8 weeks purchased from Harlan Laboratories, Indianapolis, Ind.)) were used in all experiments to evaluate the immune response to the two recombinant RB51leuB vaccine strains. All animal experimental protocols were approved by Institutional Animal Care and Use Committee (protocol # CVM-13-070) at Virginia Tech and carried out in CDC approved ABSL-3 facilities that are also AAALAC approved. For retro-orbital bleeding, mice were anaesthetized under isoflurane using Mobile Laboratory Animal Anesthesia System (Ohmeda, Madison, Wis. 53707). Mice were euthanized using overdose of carbon dioxide in-cage followed by cervical dislocation.

Preparation of Bacterial Strains:

The strains used in this study were obtained from the Brucella collection housed in the BSL-3 laboratory in Veterinary Medicine at Virginia Tech. The *Mycobacterium tuberculosis* strain H37Rv (ATCC 25618) and M *Bovis* BCG (ATCC 35734) were purchased from the American Type Culture Collection (Manassas, Va.). For preparation of the vaccine strains, four plates of leucine deficient *Brucella* minimal medium (15) were seeded with 100 ul of each strain and incubated for four days at 37° C. in 5% $CO_2$. A similar procedure using trypticase soy agar (Difco) TSA was followed for *B. abortus* 2308. Lawns of bacteria were scraped off the agar with a sterile loop and suspended in 20 ml of phosphate buffer saline (PBS). The suspensions were centrifuged at 1,962×G for 30 minutes at 4° C., washed twice with PBS, resuspended in 15% glycerol, aliquoted and stored at −80° C. until use.

For preparation of *M. tuberculosis* challenge dose, 25 ml of 7H9 Middlebrook Mycobacteria base supplemented with ADC Enrichment Medium (Difco, Becton, Dickinson and Company, Sparks, Md. 21152) were inoculated with a single colony of H37Rv strain. Culture was grown in a shaking incubator at 37° C. till the density reached 100 Klett units (mid-log phase). The strains were recovered by pelleting each culture at 1962×G for 30 minutes at 4° C. Strains were then washed twice with PBS, resuspended in 5 ml of 15% glycerol, aliquoted and stored at −80° C. until use. All strains were delivered to mice via an intraperitoneal (IP) route.

Mouse Experiment 1: Enzyme-Linked Immunoabsorbent Assay (ELISA)

A total of 9 BALB/c mice were divided into 3 experimental groups (n=3) and vaccinated IP. Group 1 was immunized with strain RB51leuB (control). Group 2 was immunized with RB51leuB expressing Ag85B. Group 3 was immunized with strain RB51leuB expressing the Rv2660c::ESAT6 fusion protein. Blood was collected from the different groups of mice by retro-orbital bleeding at weeks 3 and 6. Levels of immunoglobulin (total IgG) as well as IgG1 and IgG2a, with specificity to Ag85B and ESAT6, in serum were determined by indirect ELISA as described before [19, 20].

Mouse Experiment 2: Cytokine Proliferation Assay:

A total of 12 BALB/c mice were divided into 4 experimental groups (n=3) and vaccinated IP. Group 1 was vaccinated with 100 µl PBS (control). Group 2 was vaccinated with strain RB51leuB (control). Group 3 was vaccinated with *M. bovis* BCG. Group 4 was inoculated with an equal mix of the two RB51leuB vaccine strains (one carrying Ag85B and another carrying Rv2660c::ESAT6). The inoculation titer for the BCG group was $1\times10^6$ CFU, whereas in all RB51leuB vaccinated groups the titer was $2-4\times10^8$ CFU. Six weeks post vaccination mice were euthanized and spleens were collected for splenocyte proliferation assay as described before [21].

Mouse Experiment 3: *B. abortus* 2308 Protection Assay:

Thirty BALB/c mice were divided into 6 experimental groups (n=5) and immunized IP. Group 1 was immunized with 100 µl PBS (control). Group 2 was immunized with RB51leuB (control). Group 3 was immunized with *M. bovis* BCG strain. Group 4 was immunized with RB51leuB expressing Ag85B. Group 5 was immunized with RB51leuB expressing Rv2660c::ESAT6. Group 6 was immunized with an equal mix of the two strains of RB51leuB (one expressing Rv2660c::ESAT6 and other expressing Ag85B). The inoculation titer for the BCG group was $1\times10^5$ CFU, whereas in all strain RB51leuB vaccinated groups the titer was $2-4\times10^8$ CFU. Six weeks post vaccination, all six groups were challenged with $5\times10^4$ CFU of *B. abortus* 2308 (i.p.). Two weeks post challenge all mice were killed by $CO_2$ and cervical dislocation. Spleens and livers were removed aseptically, homogenized, serially diluted, plated on TSA agar, and incubated for four days at 37° C. in 5% $CO_2$.

Mouse Experiment 4: *M. tuberculosis* Protection Assay:

Thirty BALB/c mice were divided into 6 experimental groups (n=5). All groups were vaccinated IP with same strains and doses as those in the mouse experiment 3 study. Eight weeks post-vaccination, all nine groups were challenged with $2\times10^5$ CFU of *M. tuberculosis* (i.p.). Four weeks post-challenge all mice were killed by $CO_2$ and cervical dislocation. Spleens and lungs were removed aseptically, homogenized, serially diluted and plated on 7H10 selective media and incubated for 2-3 weeks at 37° C. in 5% $CO_2$ Mouse experiment 5: *M. tuberculosis* protection assay following subunit boosting:

Twenty BALB/c mice were divided into 4 experimental groups (n=5). Groups 1 & 2 were immunized IP with 100 µl PBS (control). Group 3 was immunized with *M. bovis* BCG strain. Group 4 with an equal mix of the two RB51leuB vaccine strains (one expressing Rv2660c::ESAT6 and another expressing Ag85B). Six weeks post-vaccination; groups 2 & 4 were boosted i.p. with 20 µg of Ag85B and 20 µg of ESAT6 in dimethyl dioctadecylammonium bromide [(DDA) (250 µg/dose; Avanti Polar Lipids, Inc.)] with 25 µg of monophosphoryl lipid A [(MPL) (Avanti Polar Lipids, Inc.)] in a volume of 100 Blood was collected from the different groups of mice by retro-orbital bleeding one week pre-boosting and post-boosting. Levels of immunoglobulin (total IgG) as well as IgG1 and IgG2a, with specificity to Ag85B and ESAT6, in serum were determined by indirect ELISA as described earlier. Two weeks post-boosting, all groups were challenged with $2\times10^5$ CFU of *M. tuberculosis* (IP). Four weeks post challenge all mice were killed by $CO_2$ and cervical dislocation. Spleens and lungs were removed aseptically, homogenized, serially diluted and plated on 7H10 selective media and incubated for 2-3 weeks at 37° C. in 5% CO?

Mouse Experiment 6: Tuberculin Skin Test & In Vitro Interferon-Gamma (INFγ) Production Responses of BALB/c Mice to Vaccination with RB51leuB Expressing *M. tuberculosis* Antigens:

Fifteen BALB/c mice were divided into 5 groups of 3 mice each (n=3) and immunized IP. Group one received PBS (control); group 2 received strain RB51leuB; group 3 received strain RB51leuB expressing Ag85B, group 4 received strain RB51leuB expressing Rv2660c::ESAT6; group 5 received an equal mix of the vaccines used in group 2 and 3. Eight weeks after vaccination, each mouse was injected with 50 ug tuberculin (PPD) into the hind leg foot-pad and swelling was measured at 24, 48 and 72 hours post exposure. Swelling was compared to the other hind leg foot-pad injected with PBS. At 96 hours mice were killed, and spleen cells were exposed to antigens in vitro to detect INF-g production using a commercially available ELISA kit (B.D. Biosciences, San Diego, Calif. 92121).

Statistical Analysis

Analysis of variance (ANOVA) was used to evaluate the differences in the protection and the production of cytokines and antibodies. Comparisons between two groups were performed with the Student's T-test. Unless otherwise stated the level of statistical significance was set at 0.05.

Results
Construction and Evaluation of Recombinant RB51 Strain Stability In Vitro Synthesized genes encoding *M. tuberculosis* protective antigens using *Brucella* codons were successfully cloned into the two expression vectors to create pNS4TrcD-rv2660c::esat6, and pNS4TrcD-ag85B for cytoplasmic expression of *M. tuberculosis* protective antigens. Western blotting confirmed expression of the synthesized genes. The GFP reporter gene cloned in frame and downstream of the synthesized mycobacterial genes was used to monitor the expression and stability of the recombinant proteins in vitro. [mycobacterial antigens::GFP] Through evaluation of GFP expression under UV light, it was found that all expression vectors were maintained for more than 15 passages or 60 days on selective medium (Table 1). When grown on non-selective enriched medium the same recombinant strains maintained the expression vector in a stable fashion up to 7-8 passages or 28-32 days (Table 1).

TABLE 1

Stability of RB51 recombinant strains carrying *M. tuberculosis* antigens along with GFP on leucine deficient medium (BMMleu) and non-selective enriched medium (TSA).

| Construct | # of Passages | # of days |
| --- | --- | --- |
| RB51leuB-TrcD-Ag85B-GFP (Selective medium) | >15 | >60 |
| RB51leuB-TrcD-Rv2660c::ESAT6-GFP (Selective medium) | >15 | >60 |
| RB51leuB-TrcD-Ag85B-GFP (non-selective enriched medium) | 7 | 28 |
| RB51leuB-TrcD-Rv2660c::ESAT6-GFP (Non-selective enriched medium) | 8 | 32 |

Evaluation of Recombinant RB51 Strains Stability in Mice

Figure 2A:
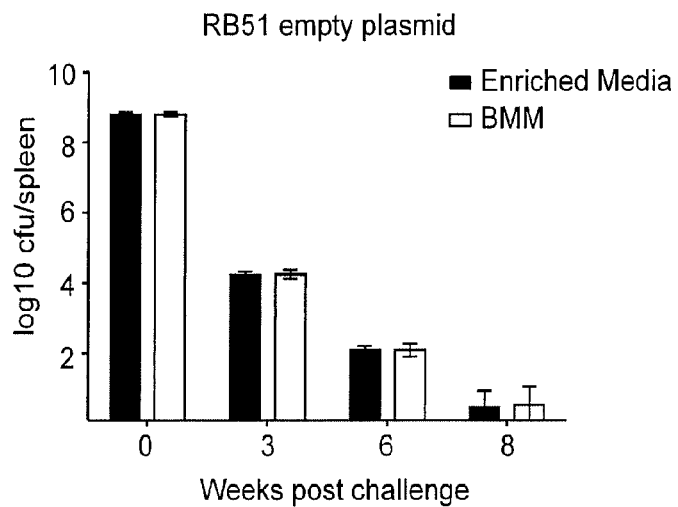
FIG. 2A-C. Stability of recombinant strains in mice. A) RB51GroE (control); B) RB51-Rv2660c-ESAT6; C) RB51-Ag85B.
Figure 2B:
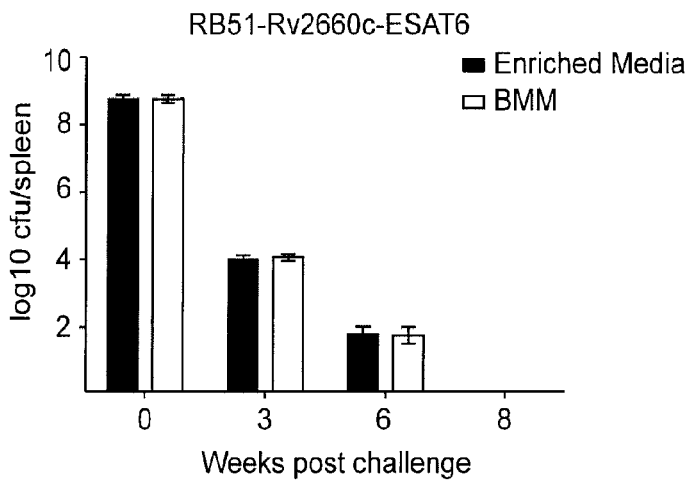
Figure 2C:
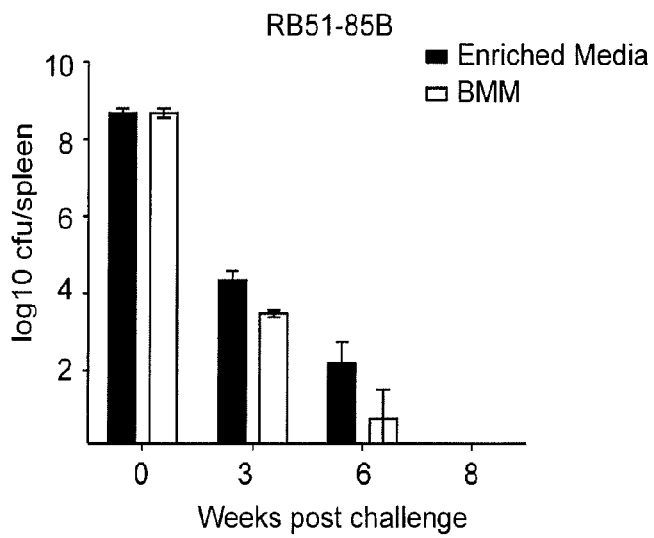

To evaluate the stability of the newly constructed vectors expressing mycobacterial antigens in strain RB51, five groups of female BALB/c mice (9 mice per group) were vaccinated IP with approximately $2\text{-}5 \times 10^8$ CFUs of strain RB51leuB carrying the constructed vectors. Three mice of each group were euthanized at 3, 6 and 8 weeks post-vaccination. All vaccinated mice cleared the vaccine strains within 6 to 8 weeks post-vaccination. The recombinant strain of RB51leuB expressing the fusion Rv2660c::ESAT6 and Ag85B maintained the vectors during the entire course of vaccine persistence, 6-8 weeks (FIGS. 2A, 2B, and 2C). Western blotting of all colonies isolated on week 6 showed stable expression of both Ag85B and fusion protein Rv2660c::ESAT6 following passage through mice.

Generation of Specific Immune Responses

Figure 3A:
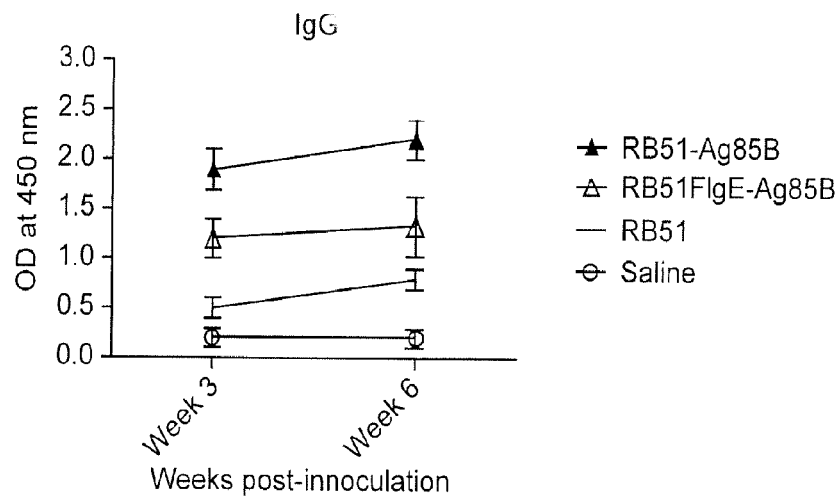
FIG. 3A-C. ELISA detection of Ag85B-specific IgG (A), IgG2a (B) and IgG1 (C) antibodies in serum of mice vaccinated with strain RB51, RB51Ag85B, RB51FlgE-Ag85B or inoculated with saline alone. FlgE constructs were developed to secrete Ag85B and Rv2660c::ESAT6 antigens. Even though these constructs were successful in secreting the antigens, they did not induce protection in these studies. Sera collected from three mice of each group at 3 and 6 weeks post-vaccination were diluted 1:100 and assayed for the presence of specific antibodies. Results were shown as the means±S.D of $OD_{450}$ of the color developed.
Figure 3B:
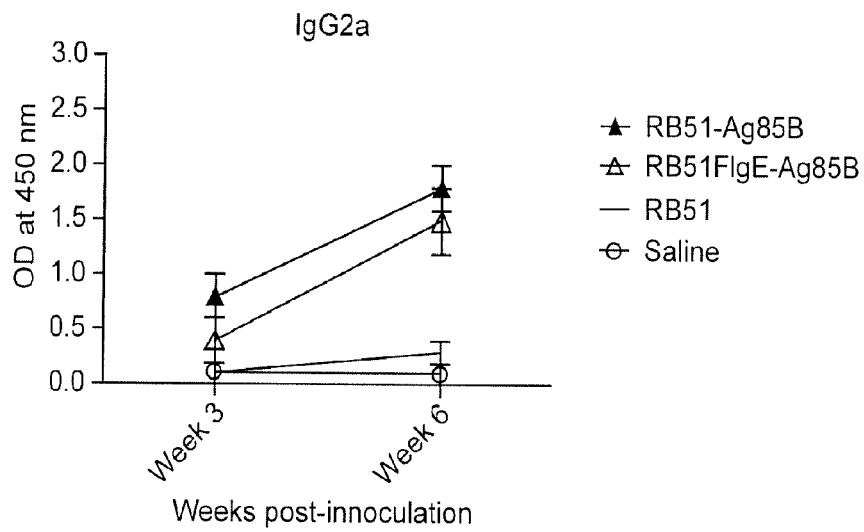
Figure 3C:
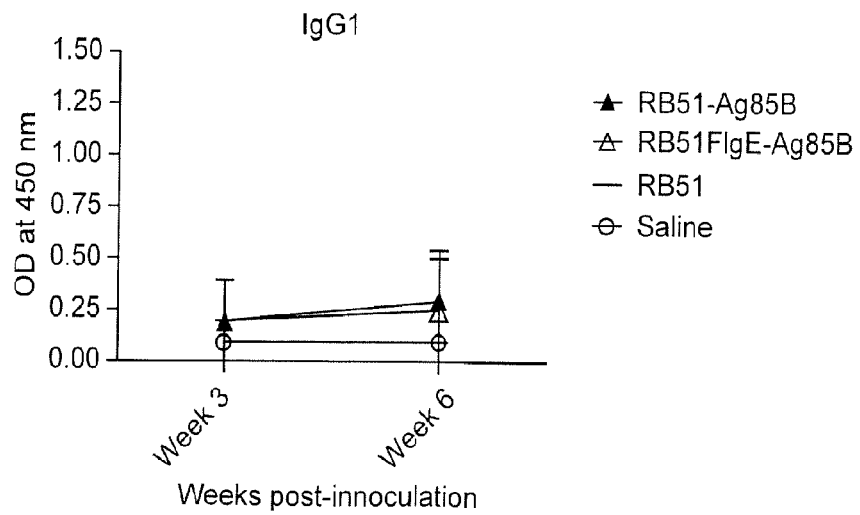

In mouse experiment 1, sera were collected from mice vaccinated at weeks three and six, and tested for the presence of serum immunoglobulin G and their isotypes (IgG, IgG1, and IgG2a) with specificity to Ag85B and ESAT6 via indirect ELISA. As expected, mice vaccinated with strain RB51leuB carrying Ag85B, but not those vaccinated with strain RB51leuB or saline, developed Ag85B-specific IgG (FIG. 3A). Upon analyzing the subisotype of IgG detected, it was shown to be predominantly IgG2a and not IgG1 (FIGS. 3B-C). Similar but lower levels of IgG and its sub-isotype IgG2a were also detected in mice vaccinated with strain RB51leuB carrying Rv2660c::ESAT6, but not in mice vaccinated with strain RB51leuB or saline (FIGS. 4A-C). Additionally, similar but higher levels of RB51-specific IgG and its serotype IgG2a were observed in all mice vaccinated with the recombinant strains of RB51 as well as the parent strain but not in mice vaccinated with saline (FIGS. 3 and 4).

Figure 5A:
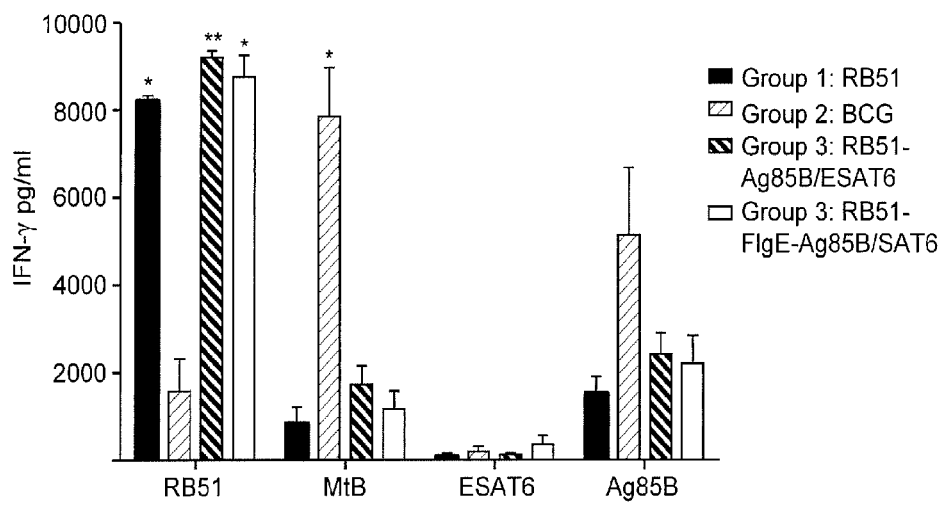
FIGS. 5A-B. Production of A) IFN-γ and B) TNF-α by splenocytes from naïve mice and mice vaccinated with strains RB51leuB, BCG, and RB51-Ag85B/Rv2660c::ESAT, RB51-Ag85B/Rv2660c::ESAT after in vitro stimulation with heat-killed RB51, heat-killed *M. tuberculosis*, Ag85B and ESAT6.

In Mouse experiment 2, total splenocytes were isolated from vaccinated mice and stimulated with heat-killed *M. tuberculosis*, heat-killed *B. abortus* RB51leuB six weeks post-vaccination. As expected, significant levels of interferon gamma (IFN-γ) were detected in mice vaccinated with RB51leuB strains and BCG when stimulated with heat killed *B. abortus* RB51leuB or *M. tuberculosis*, respectively (FIG. 5A). Similar observations, in regards to antigen specific stimulation of tumor necrosis factor-alpha (TNF-α), were made when the same groups of mice were stimulated with the antigens, however; higher levels of TNF-α were produced when splenocytes were stimulated with heat-killed *M. tuberculosis*, be it strain RB51leuB or BCG vaccinated groups possibly reflecting non-specific antigen stimulation (FIG. 5B).

Figure 5B:
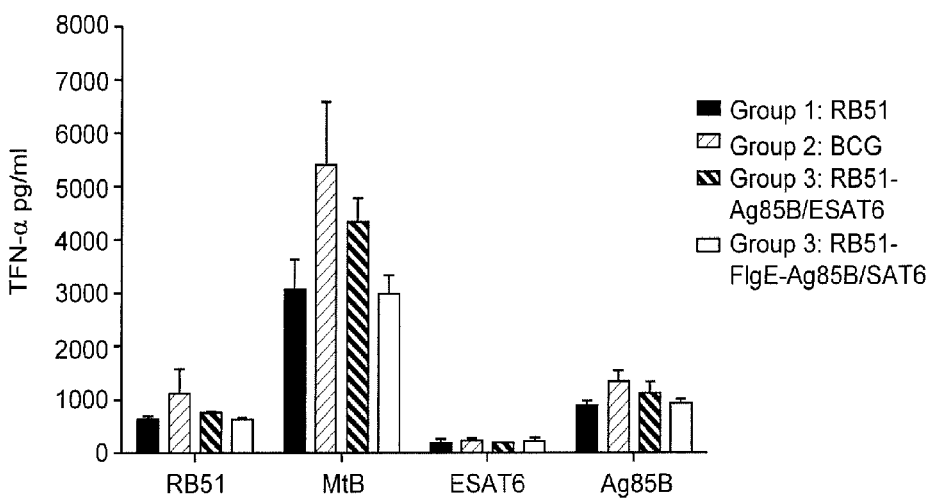

When the same splenocytes were stimulated with Ag85B, antigen specific IFN-γ and TNF-α were produced at higher levels in mice vaccinated with BCG, the mix of RB51leuB-Ag85B and RB51leuB-Rv2660c::ESAT6 than in mice vaccinated with strain RB51leuB alone (FIGS. 5A-B). However, when the same splenocytes were stimulated with ESAT6, no increase in antigen specific IFN-γ and TNF-α was observed between any of the groups (FIGS. 5A-B). No levels of IL-2, 11-4, or IL-5 were detected in the culture supernatants of splenocytes stimulated with any of the antigens.

*B. abortus* 2308 Protection Study

Figure 6A:
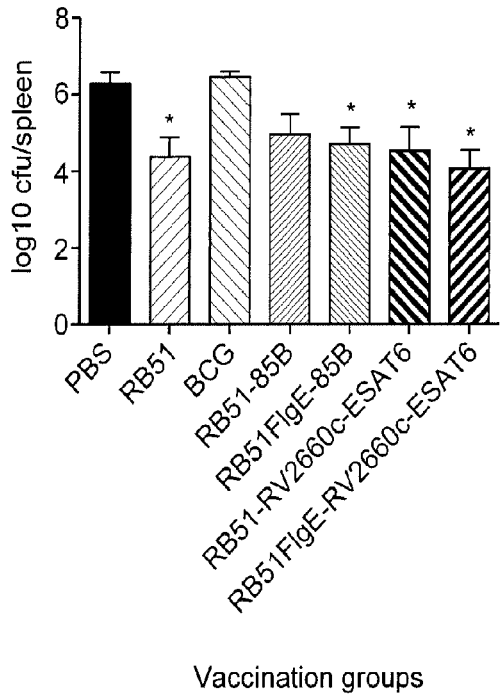
FIG. 6A-D. Resistance to *B. abortus* strain 2308 challenge infection in mice vaccinated with strains RB51leuB, BCG, and RB51-Ag85B, RB51FlgE-Ag85B, RB51-Rv2660c::ESAT6, and RB5FlgE-Rv2660c::ESAT6 (FIG. 6A). Resistance to *B. abortus* strain 2308 challenge infection in mice vaccinated with strains RB51, BCG, and combined vaccines RB51-Ag85B/Rv2660c::ESAT6 and RB51FlgE-Ag85B/Rv2660c::ESAT6 (FIG. 6B). Mice were vaccinated 6 weeks prior to the challenge infection. Two weeks post-challenge infection, the number of strain 2308 CFUs in their spleens was determined. Vaccine constructs with significant level of protection are marked with an asterisk ($P<0.05$). No significant difference was found between PBS and BCG groups. Resistance to *B. abortus* strain 2308 challenge infection in mice vaccinated with strains RB51, BCG, and RB51-Ag85B, RB51FlgE-Ag85B, RB51-Rv2660c::ESAT6, and RB51FlgE-Rv2660c-ESAT6 (FIG. 6C). Resistance to *B. abortus* strain 2308 challenge infection in mice vaccinated with strains RB51, BCG, and combined vaccines RB51-Ag85B/Rv2660c-ESAT6 and RB51FlgE-Ag85B/Rv2660c-ESAT6 (FIG. 6D). Mice were vaccinated 6 weeks prior to the challenge infection. Two weeks post-challenge infection, the number of strain 2308 CFUs in their lungs was determined. Vaccine constructs with significant level of protection are marked with an asterisk (P<0.05). No significant difference was found between PBS and BCG groups.
Figure 6B:
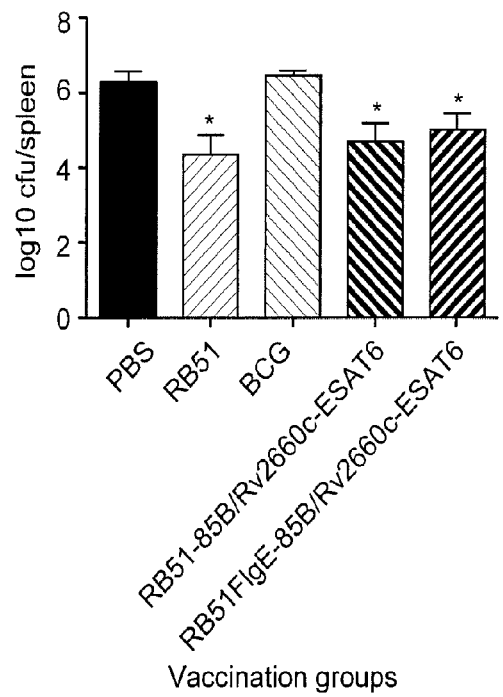
Figure 6C:
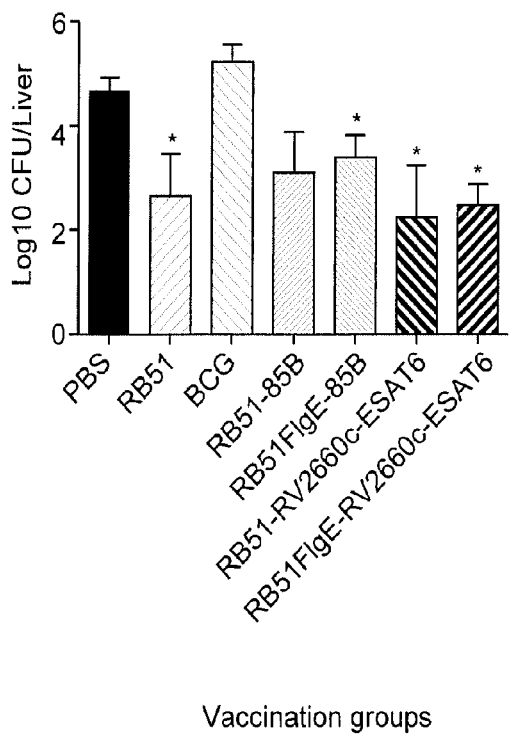
Figure 6D:
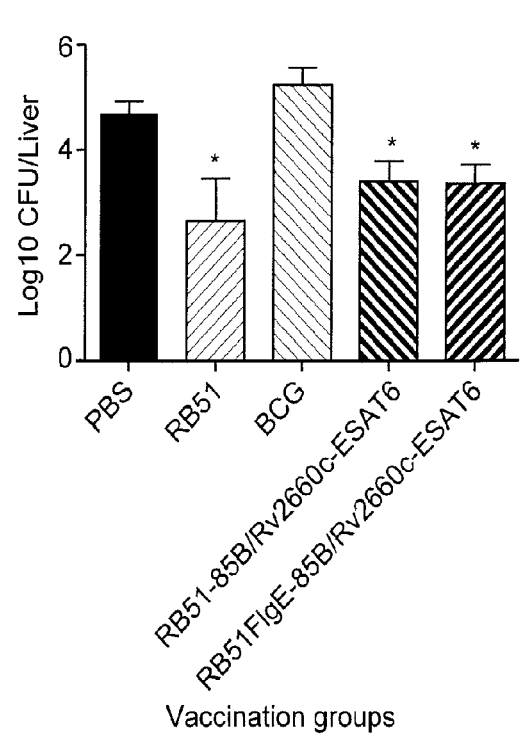

Based on colony forming units (CFU) count from homogenized spleens in Mouse Experiment 3, strains RB51leuB, RB51leuB-Rv2660c::ESAT6, and the mix of the two RB51leuB vaccine strains were able to provide significant levels of protection against subsequent challenge with *B. abortus* 2308 when compared to the unvaccinated group. Mice vaccinated with RB51leuB-Ag85B produced a 1.3 log reduction by the infection challenge with strain 2308; however this reduction was not statistically significant (p=0.09). The *M. bovis* BCG vaccinated group did not show any protection against *B. abortus* 2308 challenge (FIGS. 6A-B). Similar protection patterns were observed in the CFUs isolated from livers from the groups of mice (FIGS. 6C-D).

*M. tuberculosis* Protection Study

Mouse Experiment 4: Based on CFU count from homogenized spleens, only the BCG vaccinated group showed significant protection against *M. tuberculosis* challenge after one vaccination. Individual strains of RB51leuB expressing the Ag85B or the fusion Rv2660c::ESAT6 did not result in any level of significant protection compared to non-vaccinated group. Mice vaccinated with the mix of the two strains of RB51leuB vaccines carrying Ag85B and fusion Rv2660c::ESAT6 (Group 8) led to borderline protection (p=0.052; FIGS. 7A-D).

*M. tuberculosis* Protection Study Post-Boosting with Subunit Vaccine

Mouse Experiment 5: Serum from vaccinated mice was collected one week before and one week after boosting with Ag85B and ESAT6 to test for the presence of immunoglobulin G and its isotypes (IgG1, and IgG2a) with specificity to Ag85B and ESAT6 via indirect ELISA. Increased levels of antigens specific IgG and IgG2a were observed in mice boosted with subunit vaccines (FIGS. 8A-C and 9A-C).

Figure 10A:
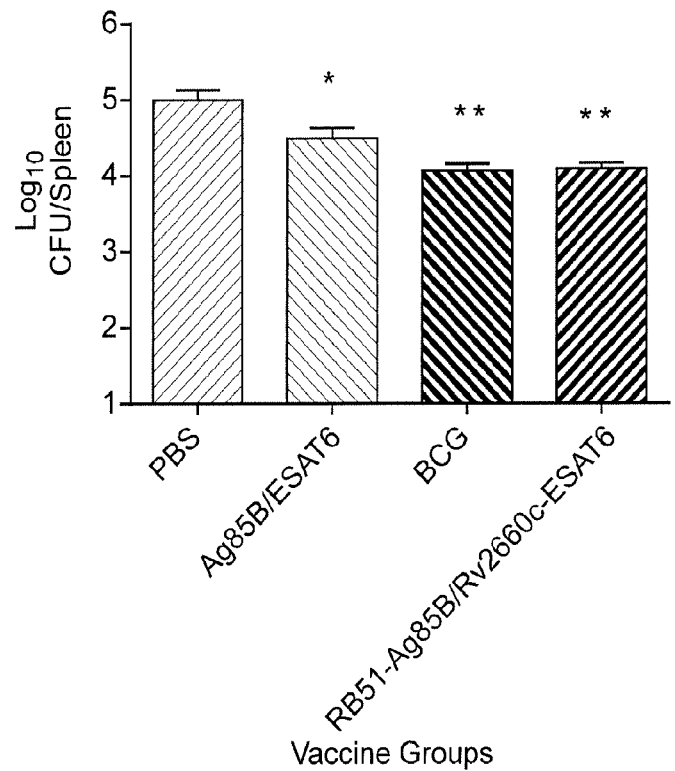
FIGS. 10A-B. *M. tuberculosis* challenge infection in mice vaccinated with BCG, and combined strains of RB51leuB carrying Ag85B and Rv2660c::ESAT6, and Ag85B/ESAT6 subunit vaccine. Mice were vaccinated for 8 weeks then boosted with subunit vaccines 2 weeks prior to the challenge infection. Four weeks post-challenge infection, the number of *M. tuberculosis* CFUs in the spleens (FIG. 10A) and lungs (FIG. 10B) were determined. Vaccine constructs with a significant level of protection are marked with one asterisk (P<0.05). Vaccine constructs marked with two asterisks provide significantly better protection than mice vaccinated with subunit vaccines only.
Figure 10B:
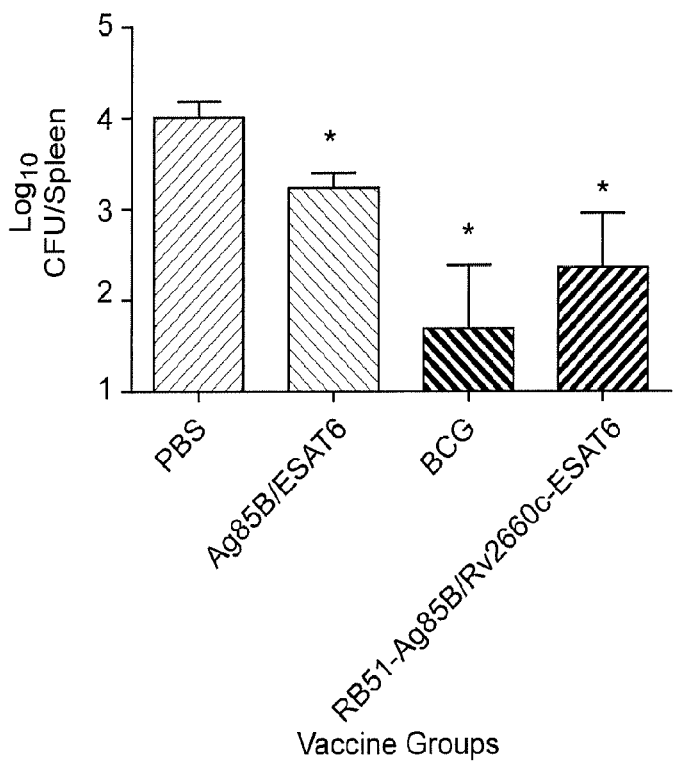

Based on CFU count from homogenized spleens, mice vaccinated with the mix of strain RB51leuB vaccines expressing Ag85B and Rv2660c::ESAT6 and subsequently boosted with proteins Ag85B and ESAT6 resulted in significant protection when compared to the PBS vaccinated group. Mice vaccinated with BCG alone gave a similar level of protection. Mice vaccinated with proteins Ag85B and ESAT6 alone demonstrated protection but it was statistically less than the protection induced by the mix of the strain RB51leuB vaccines followed by purified antigen booster (FIG. 10A). Based on CFU count from homogenized lungs, all three vaccinated groups: Ag85B/ESAT6, BCG and RB51Ag85B/Rv2660c::ESAT6 resulted in significant protection, respectively, compared to PBS vaccinated mice (FIG. 10B).

Figure 11A:
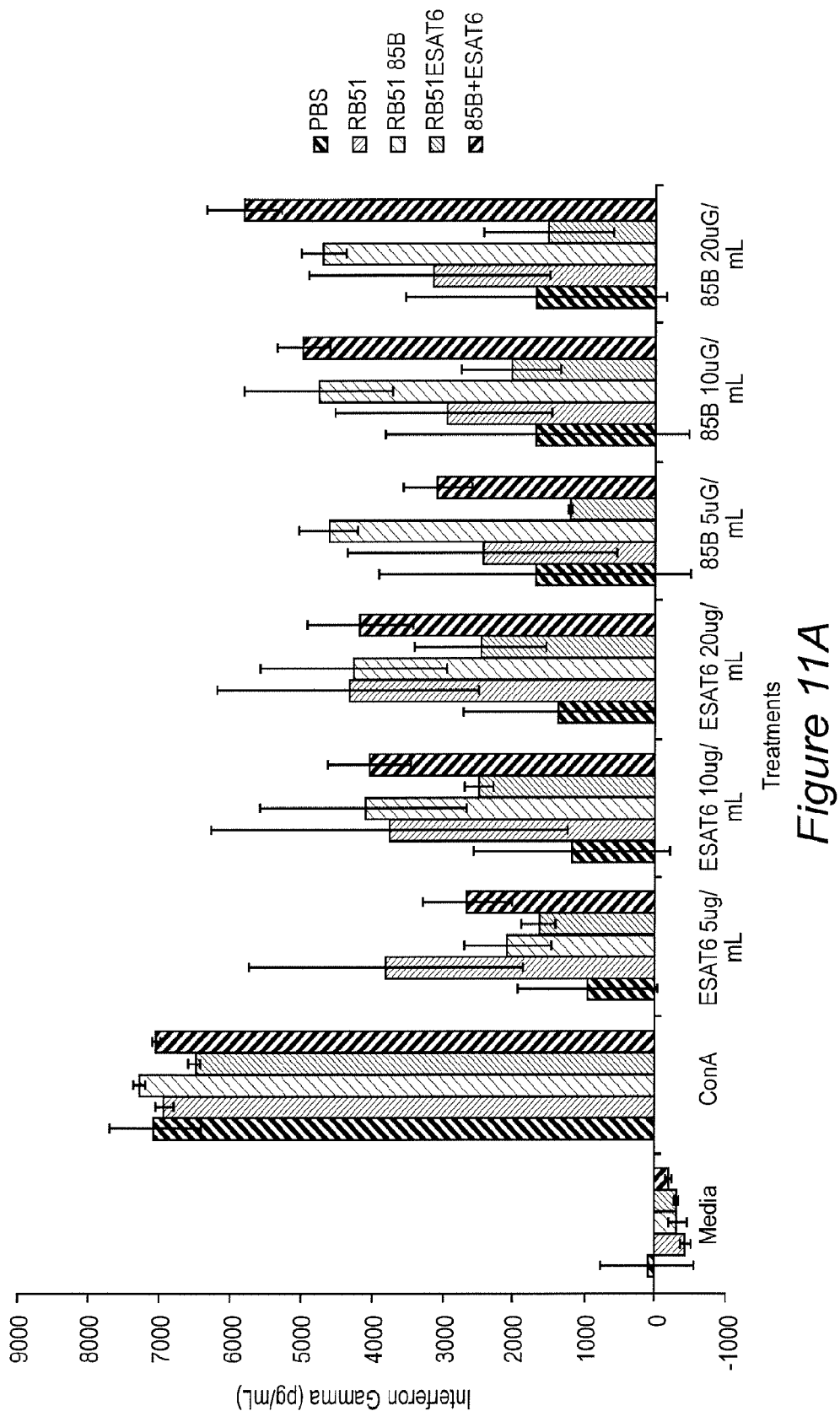
FIG. 11A-B. Level of interferon gamma secreted by splenocytes from the vaccinated mice stimulated by different treatments with various A) antigens or B) heat-killed antigens.
Figure 11B:
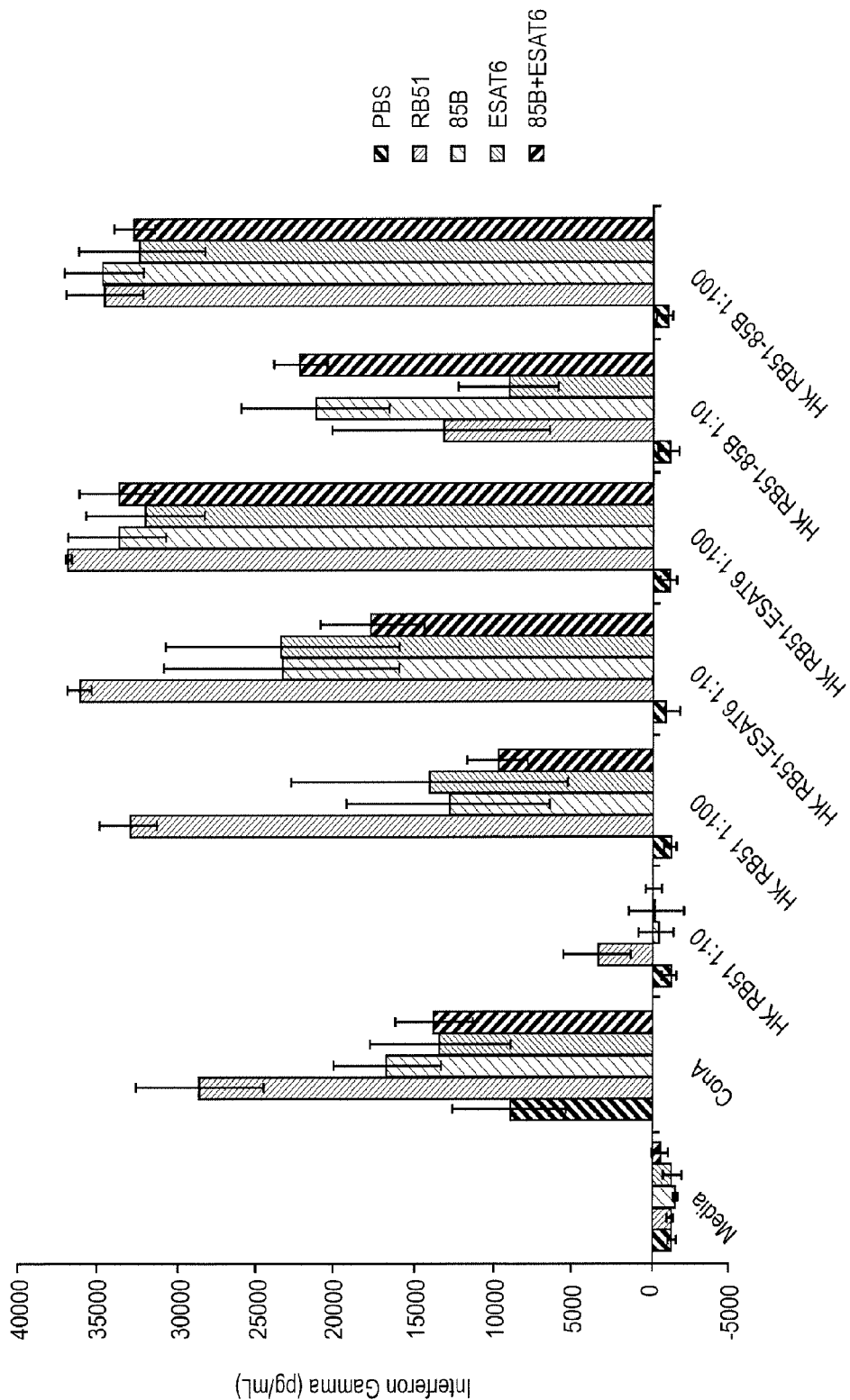

Mouse Experiment 6: The mice had no skin test response to tuberculin at 24, 48 and 72 hr post-injection. The results indicate that mice do not become tuberculin skin test positive after one vaccination with RB51leuB (group II) or one vaccination with the RB51leuB vaccine expressing 85B (group III) or ESAT-6 *M. tuberculosis* antigens (group IV) or a combination of the two heterologous expressing vaccine strains (group 5). The following antigens were used for the in-vitro stimulation of the spleen cells of each mouse to measure INF-g production: Purified 85B antigen. purified ESAT-6 antigen, heat killed RB51leuB, Con-A (positive control) and culture medium [(negative control) see FIG. 11]. As expected culture medium (negative control) gave no stimulation and Con-A (positive control) gave the highest response. Purified ESAT-6 and 85B antigens stimulated the spleen cells from all vaccinated groups to produce INF-γ above levels obtained with the PBS vaccinated mice (FIGS. 11A-B).

Discussion

*B. abortus* vaccine strain RB51 is a potent stimulator of cell-mediated immunity response. This vaccine strain acts as an immunomodulator by promoting a strong Th1 type and simultaneously inhibiting the Th2 type of immune response (5). These vaccine qualities of strain RB51 make it a good platform candidate for the development of multivalent vaccines with strong Th1 immunizing abilities. Such vaccines can confer protection against *Brucella* and other intracellular pathogens that require cell-mediated immunity for protection such as *M. tuberculosis*. In an effort to enhance these qualities, expression vector, pNS4TrcD, was created for cytoplasmic expression of mycobacterial proteins in strain RB51leuB.

Replacement of groE promoter with the trcD promoter was based on the findings of Seleem et al., [13], who showed that expression of LacZ under the trcD promoter was 2-3 times stronger than that under the groE promoter in *B. suis*. The strength of this expression was attributed to the placement of an A tract, an A+T rich upstream element, between the −38 and the −59 of the core trc promoter [22]. This enhancement in expression appeared to be due to the ability of the A tract to provide a binding site for the RNA polymerase [22, 23].

To test the functionality of the newly designed expression vector, genes encoding *M. tuberculosis* proteins; Ag85B and Rv2660c and ESAT6; were cloned into pNS4TrcD expression vector. Initially, expression of these recombinant proteins was not achieved using the original DNA sequences of *M. tuberculosis*. This lack of expression was attributed to the difference in codon usage between *Mycobacterium* species and *Brucella* species [24]. The Codon Adaptation Index (CAI) [25] was used to predict the expression level of mycobacterial proteins in strain RB51. Using CAI, it was shown that the predicted levels of expression of Ag85B, Rv2660c and ESAT6, using original DNA sequences of *M. tuberculosis*, were 0.51, 0.29 and 0.47, respectively. It has been well documented that the rate of translation of foreign antigens in high expression vectors can be influenced by their codon usage [26]. *Brucella* species have a G+C content of 57%, whereas the genomes of *Mycobacterium* species have a higher G+C content of 65.9% [27]. As a result, there is a high degree of bias for codons with G and C at the third nucleotide position, effectively, leading to codons that are rare in *Brucella* species. This use of rare codons usually compromises expression of heterologous proteins by inducing translational errors such as stalling, termination, amino acid substitution and possibly frame shifting [28]. In our study, genes coding for the intended mycobacterial genes were synthesized commercially using *Brucella* codons. Upon optimizing these codons for *Brucella* expression, the predicted levels of expression of Ag85B, Rv2660c and ESAT6 became 0.94, 0.94 and 0.93, respectively. This optimization of codon usage resulted in stable expression vectors and successful expression of *M. tuberculosis* proteins in strain RB51leuB without showing any signs of lethality or toxicity. This is the first report describing the expression of genes adapted with *Brucella* codons encoding mycobacterial proteins 85B, Rv2660c and ESAT6 in *Brucella*.

Unlike mutant strains of bacteria that are engineered for protein synthesis i.e. *Escherichia coli* HB101, expression of heterologous antigens within pathogenic strains, such as strain RB51leuB, can impose a metabolic burden. A portion of the host bacterium's energy and materials are required to maintain the foreign DNA and express foreign protein as well as maintain it without imposing toxicity on its self. In the case of recombinant vaccines, it is crucial for such strains to maintain plasmid and expression of foreign antigens in order to develop a strong immune response against the targeted antigens. One of the techniques used to assess the stability of recombinant strains in vivo and in vitro is through estimating the percentage of recombinant colonies retaining selective markers, which is used as an indicator of retention of the plasmid. However, this approach has limitations; for example, retention of selection markers does not distinguish between retention of intact vector or retention of vectors which have lost the foreign gene but retained the selective marker. Therefore a more robust confirmation is necessary not only to test for the presence of the intact expression vectors along with the foreign DNA, but also for expression of such foreign antigens. In this study, GFP was used as a reporter protein to evaluate the stability of expression vectors and expression of mycobacterial antigens in vitro. Cloning GFP in-frame downstream of the mycobacterial genes, addressed plasmid stability and mRNA translation. The ATG start codon of GFP was deleted and replaced by a linker to allow for in-frame translation and flexibility for proper GFP folding. Using this reporter system, it was shown that the recombinant strains were very stable when grown under selective pressure i.e. BMMleu. However, when grown using non-selective enriched medium, the recombinant strains were also stable up to 7-8 passages.

The stability of the constructed expression vectors was also assessed in vivo by vaccinating mice with each construct. It was apparent that recombinant strains of RB51leuB were stable for 6-8 weeks post vaccination. An immunoblot of extracts from isolated colonies at week 6 showed stable expression of the mycobacterial antigens.

In summary, the feasibility of high-level expression of heterologous proteins in strain RB51leuB has been exploited. The expression vectors constructed in this current study proved to be easily transformed into and stably maintained in strain RB51leuB. These data strongly suggest that strain RB51leuB could be used as a host for expression and delivery of protective antigens of *Mycobacterium* species. These new RB51leuB vaccine strains carrying mycobacterial antigens will serve as an environmentally safe bivalent vaccine for protection against *Brucella* and *Mycobacterium* infections simultaneously.

In an attempt to test the protective efficacy of these recombinant vaccines, a series of animal experiments were conducted; BALB/c mouse was the model of choice. This model is one of the best rodent models that can be used to evaluate both brucellosis and tuberculosis infections [29, 30]. Since *Brucella* protection studies are based on intraperitoneal vaccination followed by intraperitoneal challenge with the virulent strains, it was decided to follow the same route of vaccination and challenge for the *M. tuberculosis* protection study. Although this is not the natural route of tuberculosis infection, this route results in chronic infection in mouse spleens and lungs similar to that observed during low dose aerosol infection [31]. Additionally, this route of challenge ensures that a proper dose of the bacterium is given and also results in low levels of cross contamination between animals [31].

Using the BALB/c mouse model, a novel vaccine strategy was presented that conferred protection similar to the official tuberculosis vaccine BCG. It was hypothesized that the *B. abortus* vaccine RB51leuB carrying mycobacterial protective antigens could lead to protection against *M. tuberculosis* challenge in a murine model. Strain RB51 was chosen based on its ability to stimulate cell-mediated immunity not only against *B. abortus* challenge, but also against other heterologous proteins expressed by the strain [32-37]. However, these vaccinal qualities of strain RB51 had to be optimized for better induction of immune response against mycobacterial antigens.

Expression of mycobacterial antigens Rv2660c and ESAT6 as a fusion protein in strain RB51leuB did not affect its protective efficacy against *B. abortus* 2308 challenge. The *B. abortus* protection studies conducted showed that this recombinant RB51leuB vaccine strain induced protection against *B. abortus* 2308 challenge at levels similar to those induced by vaccine strain RB51, indicating that the expression of the heterologous fusion protein did not alter the protective efficacy of the strain. Surprisingly strain RB51leuB-85B did not protect against *Brucella* challenge at the same level.

Figure 7A:
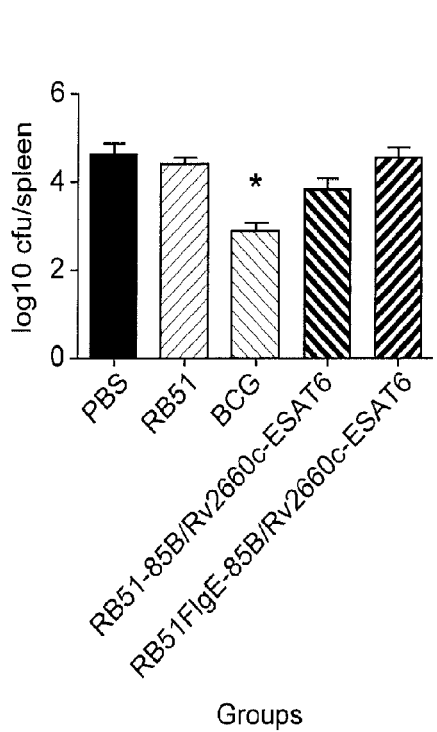
FIGS. 7A-D. Resistance to *M. tuberculosis* challenge infection in mice vaccinated with strains RB51leuB, BCG, and RB51-Ag85B, RB51FlgE-Ag85B, RB51-Rv2660c-ESAT6, and RB5FlgE-Rv2660c::ESAT6 (FIG. 7A). Resistance to *M. tuberculosis* challenge infection in mice vaccinated with strains RB51leuB, BCG, and combined vaccines RB51-Ag85B/Rv2660c::ESAT6 and RB51FlgE-Ag85B/Rv2660c::ESAT6 (FIG. 7B). Mice were vaccinated 8 weeks prior to the challenge infection. Four weeks post-challenge infection, the number of *M. tuberculosis* CFU in their spleens was determined. Vaccine constructs with significant level of protection are marked with an asterisk (P<0.05). No significant difference was found between PBS and any of the RB51leuB immunized groups. RB51-Ag85B combined with RB51-Rv2660::ESAT6 provided the best protection among all RB51leuB vaccine strains; however, the P value was 0.052. Resistance to *M. tuberculosis* challenge infection in mice vaccinated with strains RB51leuB, BCG, and RB51-Ag85B, RB51FlgE-Ag85B, RB51-Rv2660c::ESAT6, and RB51FlgE-Rv2660c::ESAT6 (FIG. 7C). Resistance to *M. tuberculosis* challenge infection in mice vaccinated with strains RB51, BCG, and combined vaccines RB51-Ag85B/Rv2660c::ESAT6 and RB5FlgE-Ag85B/Rv2660c::ESAT6 (FIG. 7D). Mice were vaccinated 8 weeks prior to the challenge infection. Four weeks post-challenge infection, the number of *M. tuberculosis* CFU in their lungs was determined. Vaccine constructs with significant level of protection are marked with an asterisk (P<0.05). No significant difference was found between PBS and any of the RB51 groups. RB51-Ag85B combined with RB51-Rv2660::ESAT6 provided the best protection among all RB51leuB vaccine strains. However, the difference was not significant.
Figure 7B:
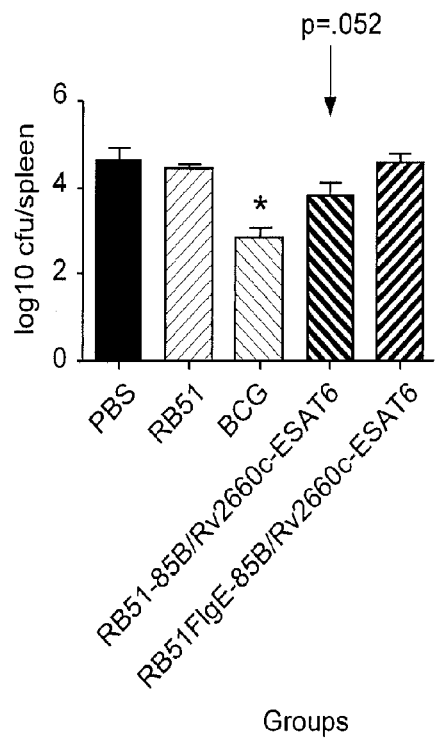
Figure 7C:
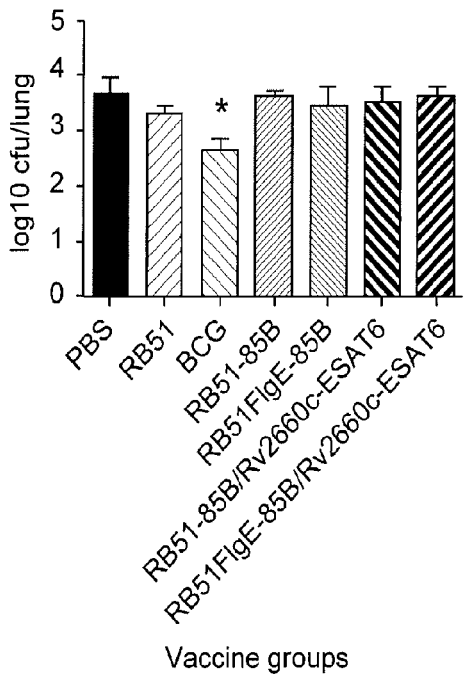
Figure 7D:
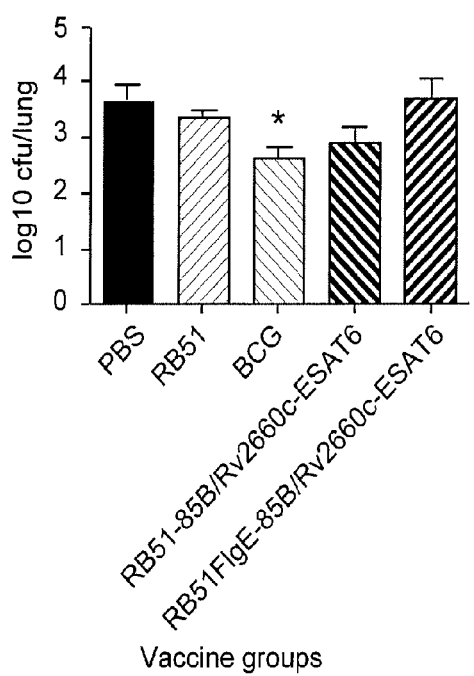
Figure 8A:
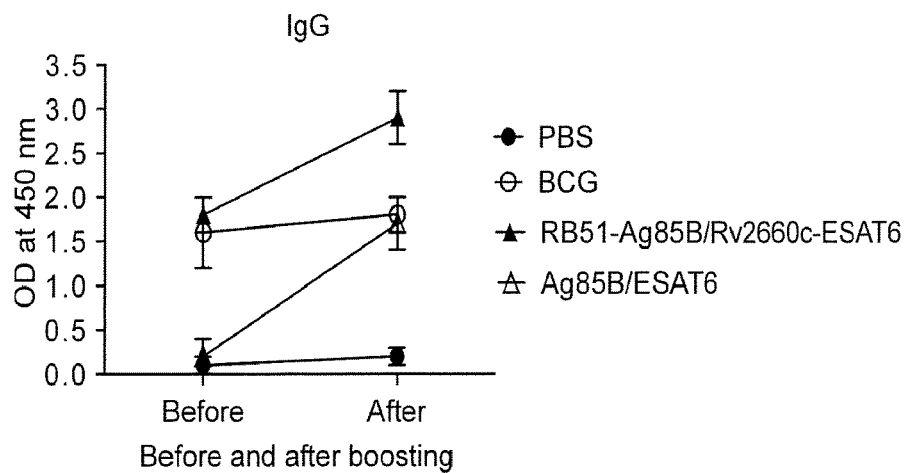
FIGS. 8A-C. ELISA detection of Ag85B-specific IgG (A), IgG2a (B) and IgG1(C) antibodies in serum of mice vaccinated BCG with combined strains of RB51 expressing Ag85B and Rv2660c::ESAT6 or inoculated with saline alone. Sera collected from each group at before and after boosting with Ag85B and ESAT6. Sera were diluted 1:100 and assayed for the presence of specific antibodies. Results were shown as the means±S.D of $OD_{450}$ of the color developed.
Figure 8B:
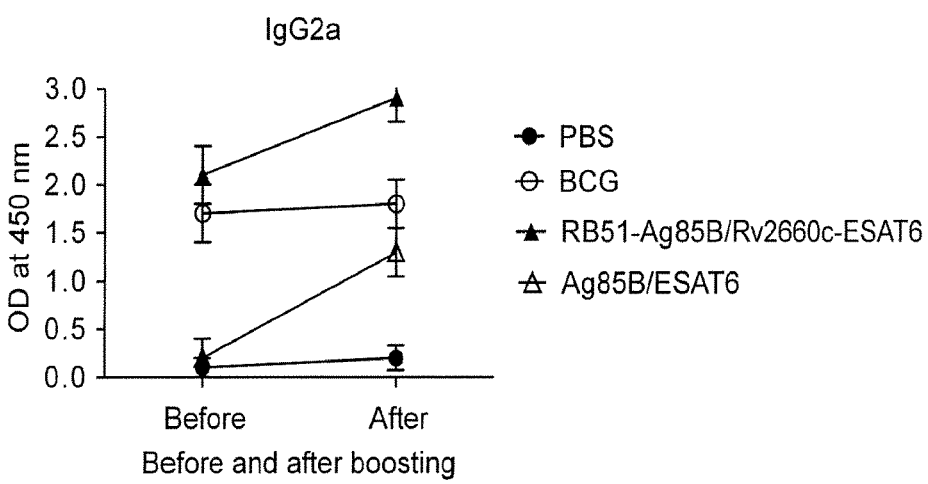
Figure 8C:
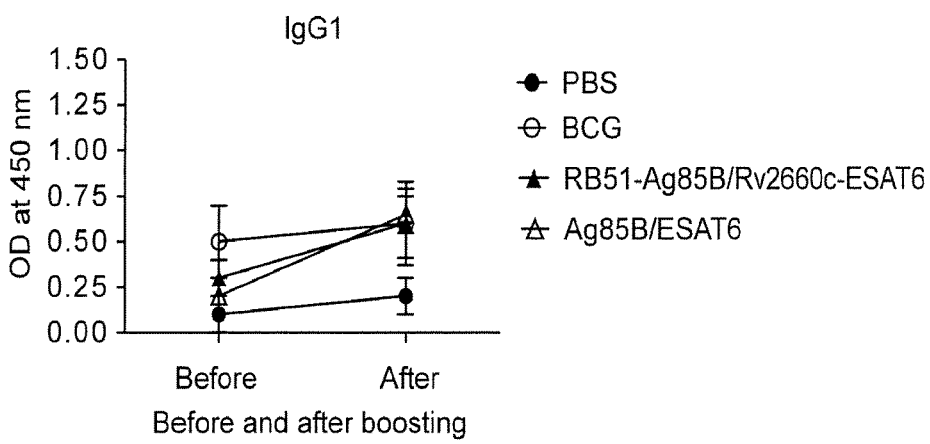
Figure 9A:
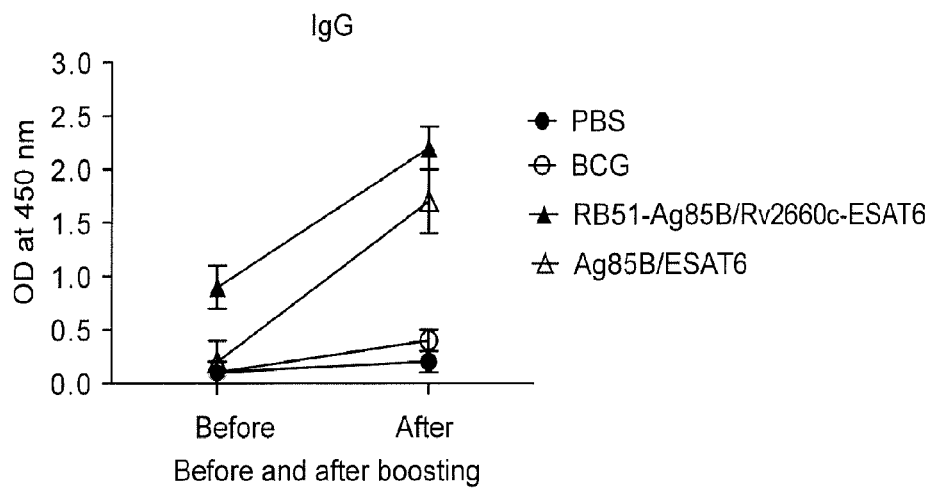
FIGS. 9A-C. ELISA detection of ESAT6-specific IgG (A), IgG2a (B) and IgG1(C) antibodies in serum of mice vaccinated BCG with combined strains of RB51leuB carrying Ag85B and Rv2660c::ESAT6 or inoculated with saline alone. Sera collected from each group at before and after boosting with Ag85B and ESAT6. Sera were diluted 1:50 and assayed for the presence of specific antibodies. Results were shown as the means±S.D of $OD_{450}$ of the color developed.
Figure 9B:
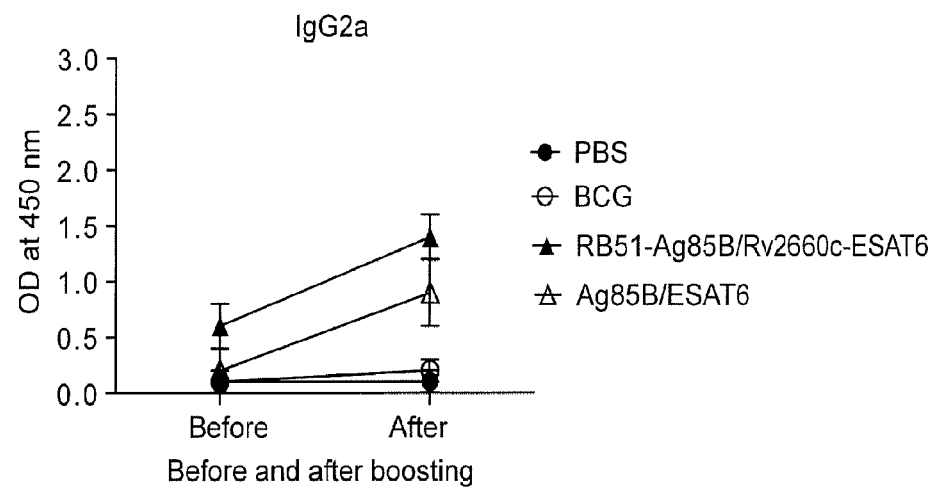
Figure 9C:
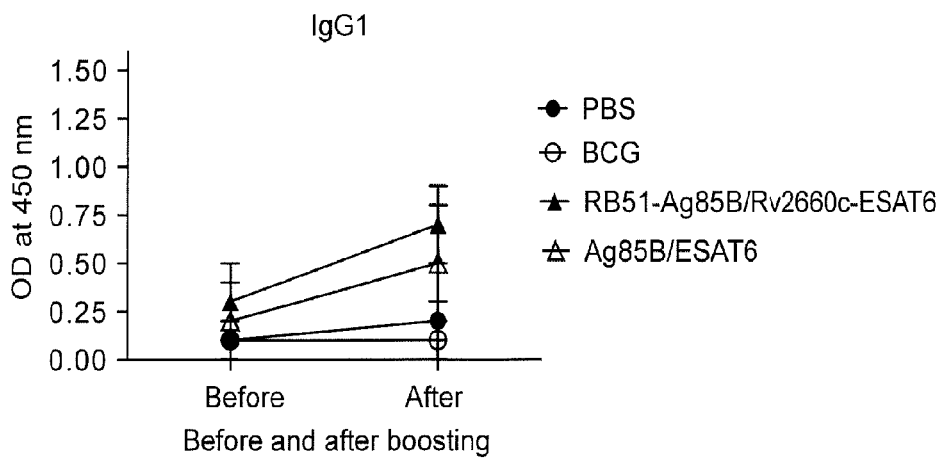

None of the individual strains of RB51leuB carrying mycobacterial antigens or a combination thereof was able to elicit protective immunity against mycobacterial challenge on their own after one vaccination. However, when the two strains of RB51leuB carrying Ag85B and Rv2660c::ESAT6 were combined, a close to significant protection level was achieved against *M. tuberculosis* challenge (FIGS. 7A-B).

Recent reports from a number of vaccine studies have shown that prime-boost protocols of immunization provide an effective strategy to promote long-term memory and strong cellular Th1 responses to *M. tuberculosis* [38-42]. In an attempt to test this strategy, another TB protection study was conducted where mice were primed with the two vaccine strains of RB51leuB carrying Ag85B and Rv2660c::ESAT6, and later boosted with a subunit vaccine consisting of purified Ag85B and ESAT6 emulsified in DDA-MPL adjuvant formulation. The protection level conferred by this vaccination strategy was essentially the same as the protection level conferred by BCG, and was higher than the protection level conferred by the subunit vaccine alone (FIG. 4.12). This clearly indicates that RB51leuB vaccine strains carrying mycobacterial antigens can be used to prime the immune system and that a single boost with a mycobacterial subunit vaccine is sufficient to confer protective immunity against *M. tuberculosis* challenge similar to that conferred by BCG. A boost with recombinant RB51leuB expressing, Rv2660c-ESAT6 fusion protein can achieve the same results. It needs to be stressed that priming with strain RB51leuB vaccines leads to protection against both *Mycobacterium* and *Brucella* infections, while the use of only purified mycobacterial proteins can lead to some protection against *Mycobacterium* infection but not *Brucella* infection.

Example 2. In Vivo Tuberculin Skin Test and In Vitro Interferon-Gamma (INF-g) Responses of BALB/c Mice to Vaccination with RB51 Expressing *Mycobacterium tuberculosis* Antigens Ag85B and/or ESAT-6

Methods

It is important that vaccines designed to protect cattle against tuberculosis and brucellosis do not interfere with official diagnostic methodologies (i.e. vaccinated animals should not respond diagnostically in a positive way to tuberculin). The skin tuberculin test is the official diagnostic test employed by USDA. Therefore, mice were administered the new vaccines as described in Example 1 and were then tested for a response to tuberculin in vivo (official diagnostic test) and INF-$\gamma$ production in vitro in order to predict a possible response to the vaccine in cattle. All work was carried out under BSL3 conditions at the CVM-BSL3 facilities of VT. Groups of 3 mice each were vaccinated with $5 \times 10(8)$ viable organisms of the following vaccine strains along with controls (see table 2).

TABLE 2

| Group | Vaccination |
|---|---|
| I | phosphate buffered saline (PBS) |
| II | RB51 |
| III | RB51 expressing *M tuberculosis* 85B antigen |
| IV | RB51 expressing *M tuberculosis* ESAT-6 antigen |
| V | RB51 expressing *M tuberculosis* 85B and RB51 expressing *M tuberculosis* ESAT-6 antigen |

Eight weeks after vaccination, each mouse was injected with tuberculin (PPD) into the hind leg foot-pad and swelling was measured at 24, 48, and 72 hours post exposure. Swelling was compared to the other hind leg foot-pad injected with PBS. At 96 hours mice were killed, and spleen cells were exposed to antigens in vitro to detect INF-g production using a commercially available ELISA kit.

Results

1. Skin test: The mice had no skin test response to tuberculin at 24, 48, and 72 hrs post-injection. The results indicate that mice do not become tuberculin skin test positive after one vaccination with strain RB51 (group II) or one vaccination with the strain RB51 vaccine expressing 85B (group III) or ESAT-6 *Mycobacterium tuberculosis* antigens (group IV) or a combination of the two heterologous expressing vaccines (group V).

Figure 12:
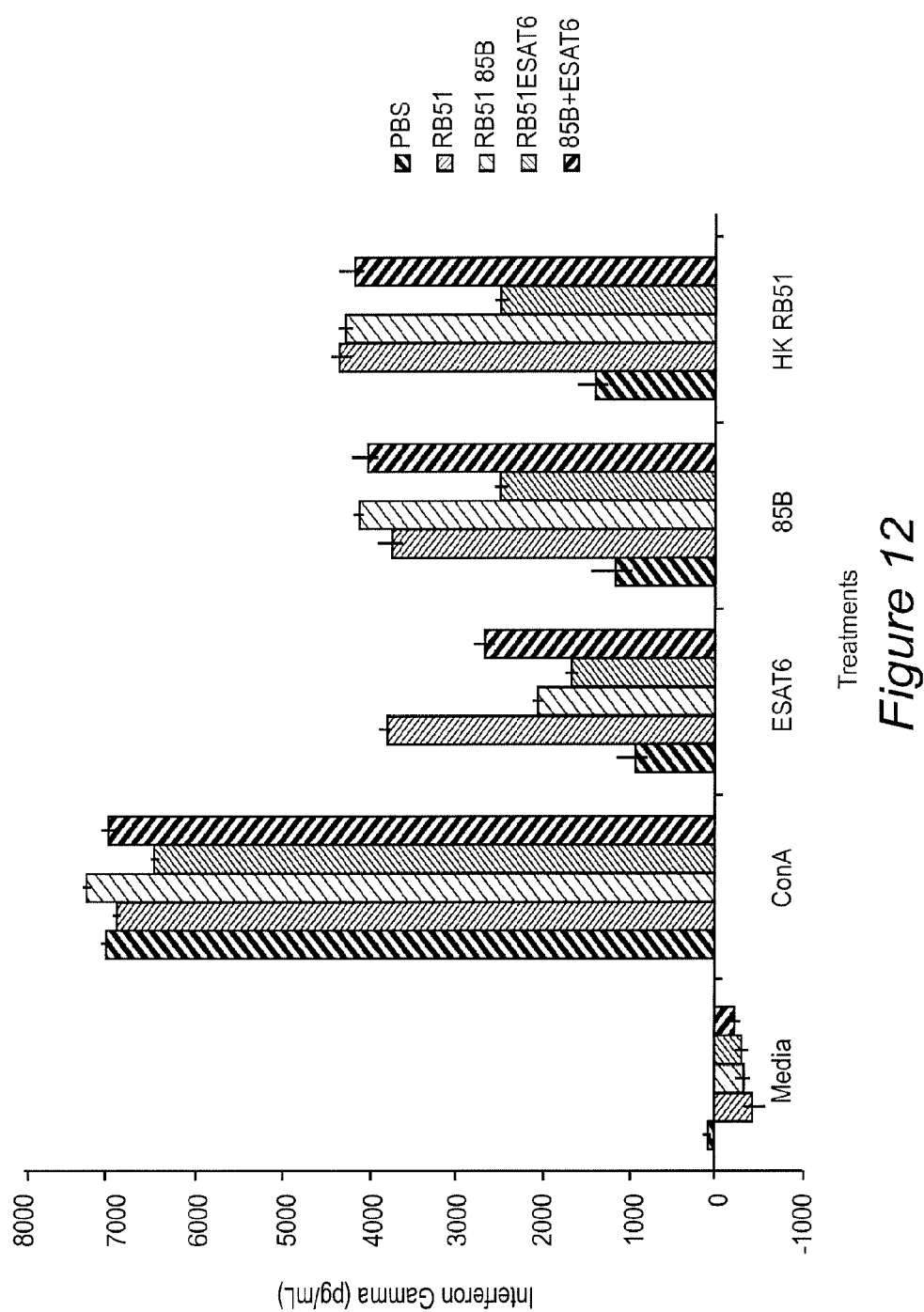
FIG. 12. Interferon-γ production by splenocytes from vaccinated mice exposed to the following antigens: Media (negative control), ConA (positive control), purified 85B, ESAT-6, and heat killed RB51 (background control for non-specific stimulation).

2. INF-g production: The following antigens were used for the in vitro stimulation of the spleen cells of each mouse: Purified 85B antigen. purified ESAT-6 antigen, heat killed RB51, Con-A (positive control) and culture media (negative control). As expected culture media (negative control) gave no stimulation and Con-A (positive control) gave the highest response. Purified ESAT-6 and 85B antigens stimulated the spleen cells from all vaccinated groups to produce INF-g above levels obtained with the PBS vaccinated mice (FIG. 12).

Conclusions

The INF-γ results indicate that vaccinated mice, including those vaccinated only with strain RB51, respond to the *M. tuberculosis* antigens 85B and ESAT-6 and would be considered positive to *Mycobacterium* exposure from a diagnostic point of view. Interestingly, mice vaccinated only with strain RB51 also responded to the TB antigens suggesting that these reactions may be non-specific and that the in vitro INF-γ test is not useful diagnostically if carried out 8-9 weeks post immunization. Alternatively, although unlikely, the mice may have become sensitized to the tuberculin utilized in the foot-pad test and therefore responded in the INF-γ assay. Tuberculin contains both, 85B and ESAT-6 antigens. Assuming that cattle would have a response similar to mice, the use of an in vitro INF-γ test (like the commercially available Bovigam test) would not be diagnostically accurate. The in vitro INF-γ test is not recognized as an official diagnostic test by USDA. Without being bound by theory, the production of INF-γ could be due to a non-specific reaction, as mice vaccinated with normal RB51 also produced INF-γ. Alternatively, the response could be due to the previous tuberculin testing.

The results presented herein suggest that one vaccination of cattle with these new vaccines will not turn them diagnostically positive to the skin test with tuberculin and therefore, these vaccines are commercially viable for use in cattle. In Example 1, it was shown that recombinant strain RB51leuB vaccines carrying mycobacterial protective antigens RV2660c and ESAT-6 as a fusion protein result in stimulation of antigens specific immune responses to mycobacterial antigens without altering the strain RB51leuB efficacy in protecting against the virulent strain of *B. abortus* 2308. In Example 2, it was shown that mice vaccinated with the recombinant strain RB51leuB vaccines did not develop a tuberculin positive skin test indicating that one vaccination does not induce a false positive diagnostic tuberculin test. The mice immunized with the recombinant strain RB51leuB vaccines were protected against *M. tuberculosis* challenge if boosted with Ag85B-EAST6 subunit vaccine along with an adjuvant. Moreover, this protection was similar to the protection obtained with BCG and better than the protection induced by one vaccination of the purified antigens. Therefore, these vaccines can protect animals such as cattle against brucellosis and prime for protection against tuberculosis without diagnostic interference with vaccine RB51leuB-RV2660c::ESAT6 and/or vaccine RB51leuB-Ag85B.

REFERENCES

1. Schurig, G. G., et al., *Biological properties of RB51; a stable rough strain of Brucella abortus*. Veterinary Microbiology, 1991. 28(2): p. 171-188.
2. Cheville N F, S. M., Jensen A E, Tatum F M, Halling S M., *Immune responses and protection against infection and abortion in cattle experimentally vaccinated with mutant strains of Brucella abortus*. American Journal of Veterinary Research, 1993. 54(10).
3. Palmer M V, O. S., Cheville N F., *Safety and immunogenicity of Brucella abortus strain RB51 vaccine in pregnant cattle*. American Journal of Veterinary Research, 1997. 58(5).
4. Vemulapalli, R., et al., *Brucella abortus RB51: enhancing vaccine efficacy and developing multivalent vaccines*. Veterinary Microbiology, 2002. 90(1-4): p. 521-532.
5. Vemulapalli, R., et al., *Brucella abortus Strain RB51 as a Vector for Heterologous Protein Expression and Induction of Specific Th1 Type Immune Responses*. Infect. Immun., 2000. 68(6): p. 3290-3296.
6. Vemulapalli, R., et al., *Overexpression of Protective Antigen as a Novel Approach To Enhance Vaccine Efficacy of Brucella abortus Strain RB51*. Infection and Immunity, 2000. 68(6): p. 3286-3289.
7. Ladel, C. H., S. Daugelat, and S. H. E. Kaufmann, *Immune response to Mycobacterium bovis bacille Calmette Guérin infection in major histocompatibility complex class I-and II-deficient knock-out mice: contribution of CD4 and CD8 T cells to acquired resistance*. European Journal of Immunology, 1995. 25(2): p. 377-384.
8. Vemulapalli, R., et al., *Reduced cerebral infection of Neospora caninum in BALB/c mice vaccinated with recombinant Brucella abortus RB51 strains expressing N. caninum SRS2 and GRA7 proteins*. Veterinary Parasitology, 2007. 148(3-4): p. 219-230.
9. Vemulapalli, R., et al., *Brucella abortus RB51: enhancing vaccine efficacy and developing multivalent vaccines*. Veterinary Microbiology, 2002. 90(1-4): p. 521-532.
10. Sanakkayala, N., et al., *Induction of Antigen-Specific Th1-Type Immune Responses by Gamma-Irradiated Recombinant Brucella abortus RB51*. Clinical and Diagnostic Laboratory Immunology, 2005. 12(12): p. 1429-1436.
11. Bandara, A. B., et al., *Brucella abortus Strain RB51 can be Used to Express Potentially Protective Antigens of Toxoplasma gondii*. Journal of Eukaryotic Microbiology, 2006. 53: p. S166-S168.
12. Ramamoorthy, S., et al., *Prevention of lethal experimental infection of C57BL/6 mice by vaccination with Brucella abortus strain RB51 expressing Neospora caninum antigens*. International Journal for Parasitology, 2007. 37(13): p. 1521-1529.
13. Seleem, M. N., et al., *Activity of native vs. synthetic promoters in Brucella*. FEMS Microbiology Letters, 2008. 288(2): p. 211-215.
14. Services, U.S.D.o.H.a.H., *Guidance for human somatic cell therapy and gene therapy*. 1998.
15. Rajasekaran, P., et al., *Brucella abortus strain RB51leucine auxotroph as an environmentally safe vaccine for plasmid maintenance and antigen overexpression*. Applied and Environmental Microbiology, 2008. 74(22): p. 7051-7055.
16. Rajasekaran, P., et al., *Over-expression of homologous antigens in a leucine auxotroph of Brucella abortus strain RB51 protects mice against a virulent B. suis challenge*. Vaccine, 2011. 29(17): p. 3106-3110.
17. Seleem, M. N., et al., *Vectors for enhanced gene expression and protein purification in Salmonella*. Gene, 2008. 421(1-2): p. 95-98.
18. Takamura, S., et al., *Ag85B of Mycobacteria Elicits Effective CTL Responses through Activation of Robust Th1 Immunity as a Novel Adjuvant in DNA Vaccine*. The Journal of Immunology, 2005. 175(4): p. 2541-2547.
19. Farinacci M, Weber S, Kaufmann S H. The recombinant tuberculosis vaccine rBCG ΔureC::hly(+) induces apoptotic vesicles for improved priming of CD4(+) and CD8 (+) T cells. Vaccine. 2012 Dec. 14; 30(52):7608-14.
20. Sun R, Skeiky Y A, Izzo A, Dheenadhayalan V, Imam Z, Penn E, Stagliano K, Haddock S, Mueller S, Fulkerson J, Scanga C, Grover A, Derrick S C, Morris S, Hone D M, Horwitz M A, Kaufmann S H, Sadoff J C. Novel recombinant BCG expressing perfringolysin O and the over-expression of key immunodominant antigens; pre-clinical characterization, safety and protection against challenge with *Mycobacterium tuberculosis*. Vaccine. 2009 Jul. 16; 27(33):4412-23.

21. Armbruster C, Junker W, Vetter N, Jaksch G. Disseminated bacille Calmette-Guérin infection in an AIDS patient 30 years after BCG vaccination. J Infect Dis. 1990 November; 162(5):1216.

22. Seleem, M. N., et al., *Establishment of a Gene Expression System in Ochrobactrum anthropi*. Appl. Environ. Microbiol., 2006. 72(10): p. 6833-6836.

23. Aiyar, S. E., R. L. Gourse, and W. Ross, *Upstream A-tracts increase bacterial promoter activity through interactions with the RNA polymerase a subunit*. Proceedings of the National Academy of Sciences, 1998. 95(25): p. 14652-14657.

24. Kane, J. F., *Effects of rare codon clusters on high-level expression of heterologous proteins in Escherichia coli*. Current Opinion in Biotechnology, 1995. 6(5): p. 494-500.
25. Puigbò, P., I. Bravo, and S. Garcia-Vallvé, *E-CAI: a novel server to estimate an expected value of Codon Adaptation Index* (*eCAI*). BMC Bioinformatics, 2008. 9(1): p. 1-7.
26. Burgess-Brown, N. A., et al., *Codon optimization can improve expression of human genes in Escherichia coli: A multi-gene study*. Protein Expression and Purification, 2008. 59(1): p. 94-102.
27. Bohlin, J., et al., *Genomic comparisons of Brucella* spp. *and closely related bacteria using base compositional and proteome based methods*. BMC Evolutionary Biology, 2010. 10(1): p. 249.
28. Dennehy, M. and A.-L. Williamson, *Factors influencing the immune response to foreign antigen expressed in recombinant BCG vaccines*. Vaccine, 2005. 23(10): p. 1209-1224.

29. Beamer G L, T. J., *Murine models of susceptibility to tuberculosis*. Archivum Immunologiae et Therapiae Experimentalis, 2005. 53(6): p. 469-83.

30. Silva, T. M. A., et al., *Laboratory Animal Models for Brucellosis Research*. Vol. 2011. 2011.

31. Biketov, S., et al., *The role of resuscitation promoting factors in pathogenesis and reactivation of Mycobacterium tuberculosis during intra-peritoneal infection in mice*. BMC Infectious Diseases: 2007. 7(1): p. 146.
32. Vemulapalli, R., et al., *Brucella abortus RB*51*: enhancing vaccine efficacy and developing multivalent vaccines*. Veterinary Microbiology: 2002. 90(1-4): p. 521-532.
33. Vemulapalli, R., et al., *Overexpression of Protective Antigen as a Novel Approach To Enhance Vaccine Efficacy of Brucella abortusStrain RB*51. Infection and Immunity, 2000. 68(6): p. 3286-3289.
34. Bandara, A. B., et al., *Brucella abortus Strain RB*51 *can be Used to Express Potentially Protective Antigens of Toxoplasma gondii*. Journal of Eukaryotic Microbiology: 2006. 53: p. S166-S168.
35. Vemulapalli, R., et al., *Brucella abortus Strain RB*51 *as a Vector for Heterologous Protein Expression and Induction of Specific Th*1 *Type Immune Responses*. Infection and Immunity: 2000. 68(6): p. 3290-3296.
36. Vemulapalli, R., et al., *Reduced cerebral infection of Neospora caninum in BALB/c mice vaccinated with recombinant Brucella abortus RB*51 *strains expressing N. caninum SRS*2 *and GRA*7 *proteins*. Veterinary Parasitology: 2007. 148(3-4): p. 219-230.
37. Kamath, A. T., et al., *Differential Protective Efficacy of DNA Vaccines Expressing Secreted Proteins of Mycobacterium tuberculosis*. Infection and Immunity: 1999. 67(4): p. 1702-1707.
38. Verreck, F. A. W., et al., *MVA.*85*A Boosting of BCG and an Attenuated, phoP Deficient M. tuberculosis Vaccine Both Show Protective Efficacy Against Tuberculosis in Rhesus Macaques*. PLoS ONE: 2009. 4(4): p. e5264.
39. McShane, H. and A. Hill, *Prime-boost immunisation strategies for tuberculosis*. Microbes and Infection: 2005. 7(5-6): p. 962-967.
40. Magalhaes, I., et al., *rBCG Induces Strong Antigen-Specific T Cell Responses in Rhesus Macaques in a Prime-Boost Setting with an Adenovirus* 35 *Tuberculosis Vaccine Vector*. PLoS ONE: 2008. 3(11): p. e3790.
41. Mollenkopf, H. J., et al., *Application of Mycobacterial Proteomics to Vaccine Design: Improved Protection by Mycobacterium bovis BCG Prime-Rv*3407 *DNA Boost Vaccination against Tuberculosis*. Infection and Immunity: 2004. 72(11): p. 6471-6479.
42. Guerrero, G. G. and C. Locht, *Recombinant HBHA Boosting Effect on BCG-Induced Immunity against Mycobacterium tuberculosis Infection*. Clinical and Developmental Immunology: 2011. 2011: p. 8.
43. Seleem et al., Enhanced expression, detection and purification of recombinant proteins using RNA stem loop and tandem fusion tags. Appl Microbiol Biotechnol (2007) 75:1385-1392.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

SEQUENCE LISTING

```
<160> NUMBER OF SEQ ID NOS: 11

<210> SEQ ID NO 1
<211> LENGTH: 306
<212> TYPE: DNA
<213> ORGANISM: Artificial Sequence
<220> FEATURE:
<223> OTHER INFORMATION: Synthetic codon-optimized ESAT6

<400> SEQUENCE: 1
ggatccatga cggaacagca gtggaatttc gccggcatcg aagccgccgc ctccgccatc     60
```

| | |
|---|---|
| cagggcaatg tgacgagcat ccatagcctc ctcgatgaag gcaagcagtc gctgaccaag | 120 |
| cttgccgcgg cctggggcgg ctcgggcagc gaagcgtatc agggcgtcca gcagaagtgg | 180 |
| gacgcgaccg ccacggaact taacaatgcg ctccagaacc tggcccgcac gatctcggaa | 240 |
| gcgggccagg cgatggcgtc cacggaaggc aatgtcacgg catgttcgc gagatcttaa | 300 |
| tctaga | 306 |

```
<210> SEQ ID NO 2
<211> LENGTH: 876
<212> TYPE: DNA
<213> ORGANISM: Artificial Sequence
<220> FEATURE:
<223> OTHER INFORMATION: Synthetic codon-optimized Ag85B

<400> SEQUENCE: 2
```

| | |
|---|---|
| ggatccttct cccgcccggg cctcccggtc gaatatctcc aggttccgtc cccgagcatg | 60 |
| ggccgcgaca tcaaggtcca gttccagtcc ggcggcaaca attcgccggc cgtctatctg | 120 |
| cttgacggcc ttcgcgcgca ggatgactat aatggctggg atatcaacac cccggccttc | 180 |
| gaatggtatt atcagagcgg cctgtccatc gtcatgccgg tgggcggcca gtcgagcttc | 240 |
| tattcggact ggtatagccc ggcctgcggc aaggcgggct gccagaccta agtgggaa | 300 |
| accctcctga cgtcggaact cccgcagtgg ctgagcgcca tcgcgcggt gaagccgacg | 360 |
| ggctccgccg cgatcggcct ctcgatggcc ggctcctcgg cgatgatcct ggccgcgtat | 420 |
| catccgcagc agttcatcta tgccggctcc ctgtcggcgc ttctcgaccc gagccagggc | 480 |
| atgggcccgt ccctgatcgg ccttgccatg ggcgatgcg gcggctataa ggccgcggat | 540 |
| atgtggggcc cgagctccga cccggcctgg gaacgcaacg atccgaccca gcagatcccg | 600 |
| aagcttgttg ccaacaatac ccgcctctgg gtctattgcg gcaacggcac gccgaatgaa | 660 |
| ctgggcggcg ccaatatccc ggcggaattc ctggaaaatt tcgtgcgctc gagcaacctt | 720 |
| aagttccagg atgcctataa cgccgcgggc ggccataacg cggttttcaa tttcccgccg | 780 |
| aacggcacgc actcgtggga atattggggc gcgcagctca atgccatgaa gggcgacctc | 840 |
| cagtcctccc tcggcgcggg cagatcttaa tctaga | 876 |

```
<210> SEQ ID NO 3
<211> LENGTH: 246
<212> TYPE: DNA
<213> ORGANISM: Artificial Sequence
<220> FEATURE:
<223> OTHER INFORMATION: Synthetic codon-optimized Rv2660c

<400> SEQUENCE: 3
```

| | |
|---|---|
| ggatccgtta tcgcgggcgt cgatcaggcg cttgcggcca cgggccaggc gtcccagcgc | 60 |
| gcggcgggcg cgtcgggcgg cgttacggtc ggcgttggcg tcggcaccga acagcgcaac | 120 |
| ctgagcgtcg tggccccgtc gcagttcacg ttctcgtccc gctcgccgga tttcgtcgat | 180 |
| gaaacggcgg gccagtcgtg gtgcgcgatc ctcggcctta tcagttcca tagatcttga | 240 |
| tctaga | 246 |

```
<210> SEQ ID NO 4
<211> LENGTH: 1147
<212> TYPE: DNA
<213> ORGANISM: Artificial Sequence
<220> FEATURE:
<223> OTHER INFORMATION: Synthetic trcD-Ag85B codon-optimized
```

<400> SEQUENCE: 4

```
gtcgaccaga aaaagatcaa aaaaatttg acaattaatc atccggctcg tataatgtgt      60
ggaattgtga gcggataaca atttcacaca ggaaacagcg ccgctgagaa aaagcgaagc    120
ggcactgctc tttaacaatt tatcagacaa tctgtgtggg cactcgaccg gaattatcga    180
ttaactttat tattaaaaat taagaggta tatattaatg tatcgattaa ataaggagga    240
ataaaccatg catcatcatc atcatcatgg tggatccttc tcccgcccgg gcctcccggt    300
cgaatatctc caggttccgt ccccgagcat gggccgcgac atcaaggtcc agttccagtc    360
cggcggcaac aattcgccgg ccgtctatct gcttgacggc cttcgcgcgc aggatgacta    420
taatggctgg gatatcaaca ccccggcctt cgaatggtat tatcagagcg gcctgtccat    480
cgtcatgccg gtgggcggcc agtcgagctt ctattcggac tggtatagcc cggcctgcgg    540
caaggcgggc tgccagacct ataagtggga aaccctcctg acgtcggaac tcccgcagtg    600
gctgagcgcc aatcgcgcgg tgaagccgac gggctccgcc gcgatcggcc tctcgatggc    660
cggctcctcg gcgatgatcc tggccgcgta tcatccgcag cagttcatct atgccggctc    720
cctgtcggcg cttctcgacc cgagccaggg catgggcccg tccctgatcg gccttgccat    780
gggcgatgcg ggcggctata aggccgcgga tatgtggggc ccgagctccg acccggcctg    840
ggaacgcaac gatccgaccc agcagatccc gaagcttgtt gccaacaata cccgcctctg    900
ggtctattgc ggcaacggca cgccgaatga actgggcggc gccaatatcc cggcggaatt    960
cctggaaaat ttcgtgcgct cgagcaacct taagttccag gatgcctata cgccgcggg   1020
cggccataac gcggttttca atttcccgcc gaacggcacg cactcgtggg aatattgggg   1080
cgcgcagctc aatgccatga agggcgacct ccagtcctcc ctcggcgcgg gcagatctta   1140
atctaga                                                             1147
```

<210> SEQ ID NO 5
<211> LENGTH: 299
<212> TYPE: PRT
<213> ORGANISM: Artificial Sequence
<220> FEATURE:
<223> OTHER INFORMATION: Synthetic trcD-Ag85B matched amino acids

<400> SEQUENCE: 5

```
Met His His His His His His Gly Gly Ser Phe Ser Arg Pro Gly Leu
1               5                   10                  15

Pro Val Glu Tyr Leu Gln Val Pro Ser Pro Ser Met Gly Arg Asp Ile
            20                  25                  30

Lys Val Gln Phe Gln Ser Gly Gly Asn Asn Ser Pro Ala Val Tyr Leu
        35                  40                  45

Leu Asp Gly Leu Arg Ala Gln Asp Asp Tyr Asn Gly Trp Asp Ile Asn
    50                  55                  60

Thr Pro Ala Phe Glu Trp Tyr Tyr Gln Ser Gly Leu Ser Ile Val Met
65                  70                  75                  80

Pro Val Gly Gly Gln Ser Ser Phe Tyr Ser Asp Trp Tyr Ser Pro Ala
                85                  90                  95

Cys Gly Lys Ala Gly Cys Gln Thr Tyr Lys Trp Glu Thr Leu Leu Thr
            100                 105                 110

Ser Glu Leu Pro Gln Trp Leu Ser Ala Asn Arg Ala Val Lys Pro Thr
        115                 120                 125

Gly Ser Ala Ala Ile Gly Leu Ser Met Ala Gly Ser Ser Ala Met Ile
    130                 135                 140
```

```
Leu Ala Ala Tyr His Pro Gln Gln Phe Ile Tyr Ala Gly Ser Leu Ser
145                 150                 155                 160

Ala Leu Leu Asp Pro Ser Gln Gly Met Gly Pro Ser Leu Ile Gly Leu
                165                 170                 175

Ala Met Gly Asp Ala Gly Gly Tyr Lys Ala Ala Asp Met Trp Gly Pro
            180                 185                 190

Ser Ser Asp Pro Ala Trp Glu Arg Asn Asp Pro Thr Gln Gln Ile Pro
        195                 200                 205

Lys Leu Val Ala Asn Asn Thr Arg Leu Trp Val Tyr Cys Gly Asn Gly
    210                 215                 220

Thr Pro Asn Glu Leu Gly Gly Ala Asn Ile Pro Ala Glu Phe Leu Glu
225                 230                 235                 240

Asn Phe Val Arg Ser Ser Asn Leu Lys Phe Gln Asp Ala Tyr Asn Ala
                245                 250                 255

Ala Gly Gly His Asn Ala Val Phe Asn Phe Pro Pro Asn Gly Thr His
            260                 265                 270

Ser Trp Glu Tyr Trp Gly Ala Gln Leu Asn Ala Met Lys Gly Asp Leu
        275                 280                 285

Gln Ser Ser Leu Gly Ala Gly Arg Ser Ser Arg
    290                 295
```

<210> SEQ ID NO 6
<211> LENGTH: 808
<212> TYPE: DNA
<213> ORGANISM: Artificial Sequence
<220> FEATURE:
<223> OTHER INFORMATION: Synthetic trcD-Rv2660C::ESAT6 codon-optimized

<400> SEQUENCE: 6

```
gtcgaccaga aaaaagatca aaaaaatttg acaattaatc atccggctcg tataatgtgt     60
ggaattgtga gcggataaca atttcacaca ggaaacagcg ccgctgagaa aaagcgaagc    120
ggcactgctc tttaacaatt tatcagacaa tctgtgtggg cactcgaccg gaattatcga    180
ttaactttat tattaaaaat taaagaggta tatattaatg tatcgattaa ataaggagga    240
ataaaccatg catcatcatc atcatcatgg tggatccgtt atcgcgggcg tcgatcaggc    300
gcttgcggcc acgggccagg cgtcccagcg cgcggcgggc gcgtcgggcg gcgttacggt    360
cggcgttggc gtcggcaccg aacagcgcaa cctgagcgtc gtggccccgt cgcagttcac    420
gttctcgtcc cgctcgccgg atttcgtcga tgaaacggcg ggccagtcgt ggtgcgcgat    480
cctcggcctt aatcagttcc atagatccat gacggaacag cagtggaatt tcgccggcat    540
cgaagccgcc gcctccgcca tccagggcaa tgtgacgagc atccatagcc tcctcgatga    600
aggcaagcag tcgctgacca agcttgccgc ggcctggggc ggctcgggca gcgaagcgta    660
tcagggcgtc cagcagaagt gggacgcgac cgccacggaa cttaacaatg cgctccagaa    720
cctggcccgc acgatctcgg aagcgggcca ggcgatggcg tccacggaag gcaatgtcac    780
gggcatgttc gcgagatctt aatctaga                                       808
```

<210> SEQ ID NO 7
<211> LENGTH: 186
<212> TYPE: PRT
<213> ORGANISM: Artificial Sequence
<220> FEATURE:
<223> OTHER INFORMATION: Synthetic trcD-Rv2660c::ESAT6 matched amino
      acids

<400> SEQUENCE: 7

```
Met His His His His His Gly Gly Ser Val Ile Ala Gly Val Asp
1               5                   10                  15

Gln Ala Leu Ala Ala Thr Gly Gln Ala Ser Gln Arg Ala Ala Gly Ala
                20                  25                  30

Ser Gly Gly Val Thr Val Gly Val Gly Val Gly Thr Glu Gln Arg Asn
            35                  40                  45

Leu Ser Val Val Ala Pro Ser Gln Phe Thr Phe Ser Ser Arg Ser Pro
    50                  55                  60

Asp Phe Val Asp Glu Thr Ala Gly Gln Ser Trp Cys Ala Ile Leu Gly
65                  70                  75                  80

Leu Asn Gln Phe His Arg Ser Met Thr Glu Gln Gln Trp Asn Phe Ala
                85                  90                  95

Gly Ile Glu Ala Ala Ala Ser Ala Ile Gln Gly Asn Val Thr Ser Ile
                100                 105                 110

His Ser Leu Leu Asp Glu Gly Lys Gln Ser Leu Thr Lys Leu Ala Ala
            115                 120                 125

Ala Trp Gly Gly Ser Gly Ser Glu Ala Tyr Gln Gly Val Gln Gln Lys
        130                 135                 140

Trp Asp Ala Thr Ala Thr Glu Leu Asn Asn Ala Leu Gln Asn Leu Ala
145                 150                 155                 160

Arg Thr Ile Ser Glu Ala Gly Gln Ala Met Ala Ser Thr Glu Gly Asn
                165                 170                 175

Val Thr Gly Met Phe Ala Arg Ser Ser Arg
            180                 185

<210> SEQ ID NO 8
<211> LENGTH: 297
<212> TYPE: PRT
<213> ORGANISM: Artificial Sequence
<220> FEATURE:
<223> OTHER INFORMATION: Synthetic protein product 6X His-tag-Ag85B

<400> SEQUENCE: 8

Met His His His His His Gly Gly Ser Phe Ser Arg Pro Gly Leu
1               5                   10                  15

Pro Val Glu Tyr Leu Gln Val Pro Ser Pro Ser Met Gly Arg Asp Ile
                20                  25                  30

Lys Val Gln Phe Gln Ser Gly Gly Asn Asn Ser Pro Ala Val Tyr Leu
            35                  40                  45

Leu Asp Gly Leu Arg Ala Gln Asp Asp Tyr Asn Gly Trp Asp Ile Asn
    50                  55                  60

Thr Pro Ala Phe Glu Trp Tyr Tyr Gln Ser Gly Leu Ser Ile Val Met
65                  70                  75                  80

Pro Val Gly Gly Gln Ser Ser Phe Tyr Ser Asp Trp Tyr Ser Pro Ala
                85                  90                  95

Cys Gly Lys Ala Gly Cys Gln Thr Tyr Lys Trp Glu Thr Leu Leu Thr
                100                 105                 110

Ser Glu Leu Pro Gln Trp Leu Ser Ala Asn Arg Ala Val Lys Pro Thr
            115                 120                 125

Gly Ser Ala Ala Ile Gly Leu Ser Met Ala Gly Ser Ser Ala Met Ile
        130                 135                 140

Leu Ala Ala Tyr His Pro Gln Gln Phe Ile Tyr Ala Gly Ser Leu Ser
145                 150                 155                 160

Ala Leu Leu Asp Pro Ser Gln Gly Met Gly Pro Ser Leu Ile Gly Leu
                165                 170                 175
```

-continued

Ala Met Gly Asp Ala Gly Gly Tyr Lys Ala Ala Asp Met Trp Gly Pro
            180                 185                 190

Ser Ser Asp Pro Ala Trp Glu Arg Asn Asp Pro Thr Gln Gln Ile Pro
        195                 200                 205

Lys Leu Val Ala Asn Asn Thr Arg Leu Trp Val Tyr Cys Gly Asn Gly
        210                 215                 220

Thr Pro Asn Glu Leu Gly Gly Ala Asn Ile Pro Ala Glu Phe Leu Glu
225                 230                 235                 240

Asn Phe Val Arg Ser Ser Asn Leu Lys Phe Gln Asp Ala Tyr Asn Ala
                245                 250                 255

Ala Gly Gly His Asn Ala Val Phe Asn Phe Pro Pro Asn Gly Thr His
            260                 265                 270

Ser Trp Glu Tyr Trp Gly Ala Gln Leu Asn Ala Met Lys Gly Asp Leu
        275                 280                 285

Gln Ser Ser Leu Gly Ala Gly Arg Ser
    290                 295

<210> SEQ ID NO 9
<211> LENGTH: 184
<212> TYPE: PRT
<213> ORGANISM: Artificial Sequence
<220> FEATURE:
<223> OTHER INFORMATION: Synthetic protein product 6X His-tag-
      Rv2660c::ESAT6

<400> SEQUENCE: 9

Met His His His His His Gly Gly Ser Val Ile Ala Gly Val Asp
1               5                   10                  15

Gln Ala Leu Ala Ala Thr Gly Gln Ala Ser Gln Arg Ala Ala Gly Ala
                20                  25                  30

Ser Gly Gly Val Thr Val Gly Val Gly Val Gly Thr Glu Gln Arg Asn
            35                  40                  45

Leu Ser Val Val Ala Pro Ser Gln Phe Thr Phe Ser Ser Arg Ser Pro
        50                  55                  60

Asp Phe Val Asp Glu Thr Ala Gly Gln Ser Trp Cys Ala Ile Leu Gly
65                  70                  75                  80

Leu Asn Gln Phe His Arg Ser Met Thr Glu Gln Gln Trp Asn Phe Ala
                85                  90                  95

Gly Ile Glu Ala Ala Ala Ser Ala Ile Gln Gly Asn Val Thr Ser Ile
            100                 105                 110

His Ser Leu Leu Asp Glu Gly Lys Gln Ser Leu Thr Lys Leu Ala Ala
        115                 120                 125

Ala Trp Gly Gly Ser Gly Ser Glu Ala Tyr Gln Gly Val Gln Gln Lys
    130                 135                 140

Trp Asp Ala Thr Ala Thr Glu Leu Asn Asn Ala Leu Gln Asn Leu Ala
145                 150                 155                 160

Arg Thr Ile Ser Glu Ala Gly Gln Ala Met Ala Ser Thr Glu Gly Asn
                165                 170                 175

Val Thr Gly Met Phe Ala Arg Ser
            180

<210> SEQ ID NO 10
<211> LENGTH: 42
<212> TYPE: DNA
<213> ORGANISM: Artificial Sequence
<220> FEATURE:
<223> OTHER INFORMATION: Synthetic primer

```
<400> SEQUENCE: 10
gggaagcttg ggtctagaag tttcgctcgc ggtgagtggc ga                              42

<210> SEQ ID NO 11
<211> LENGTH: 30
<212> TYPE: DNA
<213> ORGANISM: Artificial Sequence
<220> FEATURE:
<223> OTHER INFORMATION: Synthetic primer

<400> SEQUENCE: 11
gggactagtt caggccgaaa gtgccttgaa                                            30
```

We claim:

1. A multivalent vaccine or immunogenic composition, comprising
at least one *Brucella* strain transformed with a vector expressing at least one *M. tuberculosis* antigen, wherein said at least one *M. tuberculosis* antigen is codon optimized for expression in said at least one *Brucella* strain and wherein said at least one *M. tuberculosis* antigen comprises at least one of Ag85B and Rv2660c, and
a vehicle or carrier suitable for administration to a subject.

2. The multivalent vaccine or immunogenic composition of claim 1, wherein said at least one *Brucella* strain is *B. abortus* strain RB51leuB.

3. The multivalent vaccine or immunogenic composition of claim 1, wherein said at least one *M. tuberculosis* antigen is Ag85B.

4. The multivalent vaccine or immunogenic composition of claim 1, wherein said at least one *M. tuberculosis* antigen is Rv2660c and ESAT6.

5. The multivalent vaccine or immunogenic composition of claim 4, wherein Rv2660c and ESAT6 are expressed as a fusion protein.

6. The multivalent vaccine or immunogenic composition of claim 1, wherein said vaccine includes
a first *Brucella* strain transformed with a vector expressing Ag85B and
a second *Brucella* strain transformed with a vector expressing Rv2660c and ESAT6.

7. A multivalent vaccine or immunogenic composition, comprising
at least one *Brucella* strain transformed with a vector expressing at least one *Mycobacterium* antigen, wherein said at least one *Mycobacterium* antigen is codon optimized for expression in said at least one *Brucella* strain and wherein said vector includes a TrcD promoter, and
a vehicle or carrier suitable for administration to a subject.

8. The multivalent vaccine or immunogenic composition of claim 7, wherein said at least one *Mycobacterium* antigen is encoded by a sequence selected from the group consisting of SEQ ID NO: 1, SEQ ID NO: 2, and SEQ ID NO: 3.

9. A chimeric *Brucella* strain comprising one or more sequences coding for at least one *M. tuberculosis* antigen, wherein said at least one *M. tuberculosis* antigen comprises at least one of Ag85B and Rv2660c and wherein said at least one *M. tuberculosis* antigen is codon optimized for expression in said *Brucella*.

10. The chimeric *Brucella* strain of claim 9, wherein said *Brucella* is *B. abortus* strain RB51leuB.

11. The chimeric *Brucella* strain of claim 9, wherein said at least one *Mycobacterium* antigen is Ag85B.

12. The chimeric *Brucella* strain of claim 9, wherein said at least one *Mycobacterium* antigen is Rv2660c and ESAT6.

13. A chimeric *Brucella* strain comprising one or more sequences coding for at least one *Mycobacterium* antigen, wherein said *Brucella* strain is engineered with a TrcD promoter.

14. The chimeric *Brucella* strain of claim 13, wherein said one or more sequences coding for at least one *Mycobacterium* antigen is selected from the group consisting of SEQ ID NO: 1, SEQ ID NO: 2, and SEQ ID NO: 3.

15. A plasmid comprising a sequence selected from the group consisting of SEQ ID NO: 4 and SEQ ID NO: 6.

16. A method for protecting or treating a subject at risk of or suffering from at least one disease caused by one or more bacterium, said method comprising administering to said subject an effective amount of the vaccine or immunogenic composition of claim 1.

17. The method of claim 16, further comprising the step of administering at least one purified polypeptide comprising at least one of Ag85B, Rv2660c, and ESAT6.

18. The method of claim 17, wherein said subject is administered a first purified polypeptide comprising Ag85B and a second purified polypeptide comprising ESAT6.

19. The method of claim 16, wherein said at least one disease is brucellosis and/or tuberculosis.

20. The method of claim 19, wherein said one or more bacterium is *B. abortus* and/or *M. tuberculosis*.

21. The method of claim 16, wherein said subject is selected from the group consisting of humans, cows, sheep, goats, pigs, bison, elk, camels, dogs, and poultry.

22. The method of claim 21, wherein said subject is a cow.

23. A method of raising an immune response to both *Mycobacterium* and *Brucella* in a subject, said method comprising the step of administering to said subject a chimeric *Brucella* strain as set forth in claim 9.

24. The method of claim 23, further comprising a step of administering to said subject a booster a period of time after said administering step, said booster including one or more *Mycobacterium* antigens or one or more nucleotides coding for said one or more *Mycobacterium* antigens.

* * * * *